US008398849B2

(12) United States Patent
Cross et al.

(10) Patent No.: US 8,398,849 B2
(45) Date of Patent: *Mar. 19, 2013

(54) APPLICATION OF VISBREAKER ANALYSIS TOOLS TO OPTIMIZE PERFORMANCE

(75) Inventors: Collin Wade Cross, Spring, TX (US); Andre Vanhove, Beveren (BE); David Owen, Hawarden (GB)

(73) Assignee: General Electric Company, Schenectady, NY (US)

( * ) Notice: Subject to any disclaimer, the term of this patent is extended or adjusted under 35 U.S.C. 154(b) by 594 days.

This patent is subject to a terminal disclaimer.

(21) Appl. No.: 12/630,345

(22) Filed: Dec. 3, 2009

(65) Prior Publication Data
US 2010/0116715 A1      May 13, 2010

Related U.S. Application Data

(63) Continuation-in-part of application No. 11/456,128, filed on Jul. 7, 2006, now Pat. No. 7,740,750, which is a continuation-in-part of application No. 11/178,846, filed on Jul. 11, 2005, now Pat. No. 7,394,545.

(51) Int. Cl.
*C10G 9/16* (2006.01)
(52) U.S. Cl. .................................. 208/255; 208/48 AA
(58) Field of Classification Search .................. None
See application file for complete search history.

(56) References Cited

U.S. PATENT DOCUMENTS

| | | | |
|---|---|---|---|
| 3,449,586 A | 6/1969 | Serra | |
| 3,952,580 A | 4/1976 | Bennett | |
| 4,362,386 A | 12/1982 | Matsushita et al. | |
| 4,575,413 A | 3/1986 | Pizzoni et al. | |
| 4,927,519 A | 5/1990 | Forester | |
| 5,143,594 A | 9/1992 | Stephenson et al. | |
| 5,309,213 A | 5/1994 | Desjardins et al. | |
| 5,412,581 A | 5/1995 | Tackett | |
| 5,504,573 A | 4/1996 | Cheiky-Zelina | |
| 7,127,356 B2 | 10/2006 | Nicoli et al. | |
| 2005/0133211 A1 | 6/2005 | Osborn et al. | |
| 2006/0073013 A1 | 4/2006 | Emigholz et al. | |
| 2007/0008540 A1 | 1/2007 | Vanhove et al. | |
| 2009/0100912 A1 | 4/2009 | Butler et al. | |
| 2010/0038286 A1 | 2/2010 | Greaney et al. | |

FOREIGN PATENT DOCUMENTS

| | | |
|---|---|---|
| EP | 0 321 424 B1 | 3/1993 |
| EP | 0 529 397 B1 | 7/1995 |
| EP | 0 768 363 B1 | 12/1999 |
| JP | 06201592 A | 7/1994 |
| JP | 09304412 A | 11/1997 |
| WO | WO2007008787 A2 | 1/2007 |
| WO | WO2007008787 A2 | 1/2007 |
| WO | W02008076570 A3 | 6/2008 |

(Continued)

OTHER PUBLICATIONS

PCT International Search Report and Written Opinion issued in connection with corresponding International Application No. PCT/US2010/054911 on Mar. 29, 2011.

(Continued)

*Primary Examiner* — Tam M Nguyen
(74) *Attorney, Agent, or Firm* — Wegman Hessler & Vanderburg

(57) ABSTRACT

A system and method are outlined for controlling and optimizing chemical injection into a process unit to control fouling. The method uses an optical device to measure the fouling propensity of the process fluid at various points within the process unit. The measurements are compared with one another and prediction methods are used to evaluate the fouling potential within the unit, and determine the proper chemical dosage. Antifoulant chemical is then introduced into the unit to control the rate of fouling. The method and application continue on a frequent basis to maintain optimal fouling control within the unit.

22 Claims, 19 Drawing Sheets

FOREIGN PATENT DOCUMENTS

| WO | WO2008076570 | A2 | 6/2008 |
|----|--------------|----|--------|
| WO | WO2008076570 | A2 | 6/2008 |
| WO | WO2008076570 | A3 | 6/2008 |
| WO | WO2008076570 | A3 | 6/2008 |

OTHER PUBLICATIONS

Mettler Toledo, Advancing Flow Assurance Research with in Situ Particle Measurement, 1 pg.
Mettler Toledo, Asphalteness, Waxes, Emulsions, and Oil Suspensions: Inline Particle and Droplet Measurements, 1 pg.
Mettler Toledo, C35 Ensure Targeted Granule Size in Real Time, 2 pgs.
Mettler Toledo, Detecting process upsets with in-process video microscopy, 1 pg.
Mettler Toledo, Gas Bubbles and Three-Phase Systems, 1 pg.
Mettler Toledo, iC FBRM Software, Particle System Characterization, 2 pgs.
Mettler Toledo, Oil Sands, 1 pg.
Mettler Toledo, Particle and Droplet Processing, 1 pg.
Mettler Toledo, Particle Characterization: Crystals, Particles, and Droplets, 1 pg.
Mettler Toledo, PetrochemicalsNews 5, Optimizing Oil Production, 1 pg.
Mettler Toledo, Crystals, Particles and Droplets, Measurement for Real-Time Optimization, 12 pgs.
Mettler Toledo, PVM technology, Particulate Process Understanding, 4 pgs.
Mettler Toledo, Research in Flow Assurance, 1 pg.
Mettler Toledo, Solids and Droplets in Crude Oil, 1 pg.
Mettler Toledo, V819, Process Analytical Technology, 2 pgs.
Mettler Toledo, Advancing Flow Assurance Research with in Situ Particle Measurement, 1 pg., Nov. 2009.
Mettler Toledo, Asphalteness, Waxes, Emulsions, and Oil Suspensions: Inline Particle and Droplet Measurements, 1 pg., Nov. 2009.
Mettler Toledo, C35 Ensure Targeted Granule Size in Real Time, 2 pgs., Oct. 2008.
Mettler Toledo, Detecting process upsets with in-process video microscopy, 1 pg. Nov. 2009.
Mettler Toledo, Gas Bubbles and Three-Phase Systems, 1 pg., Nov. 2009.
Mettler Toledo, iC FBRM Software, Particle System Characterization, 2 pgs., Nov. 2009.
Mettler Toledo, Oil Sands, 1 pg., Nov. 2009.
Mettler Toledo, Particle and Droplet Processing, 1 pg., Nov. 2009.
Mettler Toledo, Particle Characterization: Crystals, Particles, and Droplets, 1 pg., Sep. 2007.
Mettler Toledo, PetrochemicalsNews 5, Optimizing Oil Production, 1 pg., Feb. 2009.
Mettler Toledo, Crystals, Particles and Droplets, Measurement for Real-Time Optimization, 12 pgs., Feb. 2009.
Mettler Toledo, PVM technology, Particulate Process Understanding, 4 pgs., Mar. 2007.
Mettler Toledo, Research in Flow Assurance, 1 pg., Nov. 2009.
Mettler Toledo, Solids and Droplets in Crude Oil, 1 pg., Nov. 2009.
Mettler Toledo, V819, Process Analytical Technology, 2 pgs., May 2008.

| INPUT | | |
|---|---|---|
| Sample | 20.0 gr | |
| Pv min | 1.01 | Samples No. 5 |
| Pv max | 1.20 | |
| | 0.19 | 4 |

| Sample | Pv Tested | Heptane(ml) | Real Sample (gr) | Real Pv Tested | VFM #part/cm | VFM value |
|---|---|---|---|---|---|---|
| 0 | 1.000 | 0.000 | 20.05 | 1.000 | 625 | |
| 1 | 1.010 | 0.089 | 19.92 | 1.010 | 648 | |
| 2 | 1.058 | 0.509 | 20.00 | 1.058 | 710 | |
| 3 | 1.105 | 0.929 | 20.10 | 1.104 | 952 | |
| 4 | 1.153 | 1.350 | 20.00 | 1.153 | 850 | |
| 5 | 1.200 | 1.770 | 20.10 | 1.199 | 800 | |
| 6 | | | | | | |
| 7 | | | | | | |
| 8 | | | | | | |

Pv Test

VFM Analysis With/Without Treatment
| Azeri% | 1hr at Room Temperature | 10ppm 7R30E 1hr at Room Temperature | Assuming NO interaction | Interaction | Interaction with 7R30E | 7R30E effect |
|---|---|---|---|---|---|---|
| 0 | 203 | 200 | 203 | 0 | -3 | -3 |
| 10 | 248 | 230 | 194.1 | 53.9 | 35.9 | -18 |
| 20 | 274 | 247 | 185.2 | 88.8 | 61.8 | -27 |
| 40 | 270 | 255 | 167.4 | 102.6 | 87.6 | -15 |
| 60 | 335 | 307 | 149.6 | 185.4 | 157.4 | -28 |
| 80 | 203 | 207 | 131.8 | 71.2 | 75.2 | 4 |
| 100 | 114 | 120 | 114 | 0 | 6 | 6 |
FIG. 20
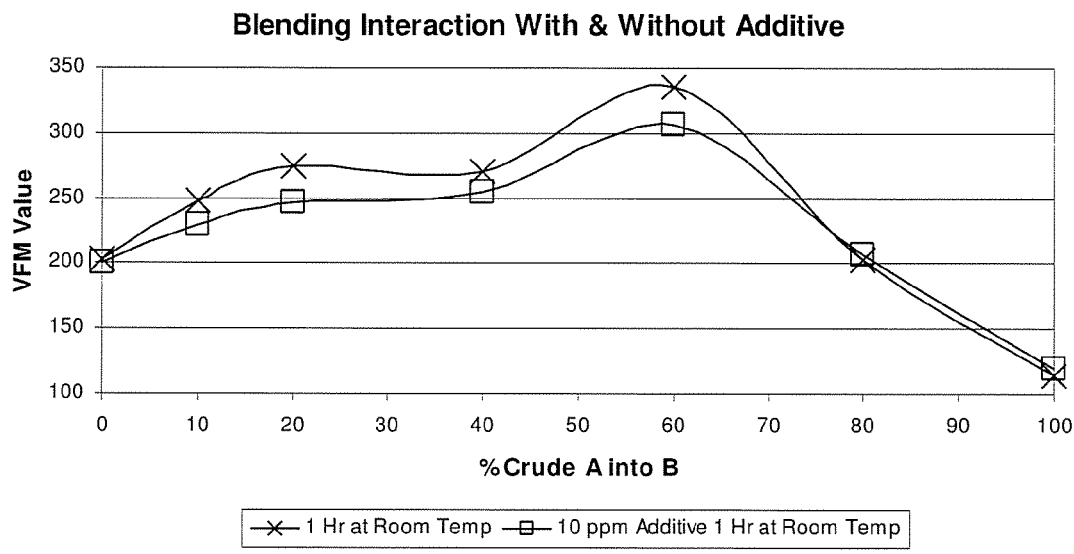
FIG. 21
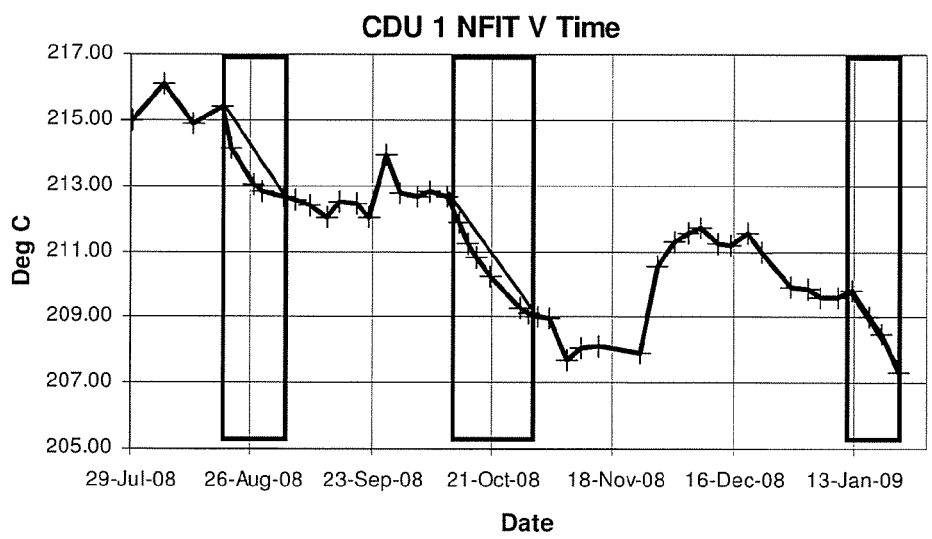
FIG. 22

APPLICATION OF VISBREAKER ANALYSIS TOOLS TO OPTIMIZE PERFORMANCE

CROSS REFERENCE TO RELATED APPLICATIONS

This application is a continuation-in-part of U.S. patent application Ser. No. 11/456,128 filed Jul. 7, 2006, now allowed, now U.S. Patent No. 7,740,750. which was, in turn, a continuation-in-part of U.S. patent application Ser. No. 11/178,846 filed Jul. 11, 2005 now U.S. Pat. No. 7,394,545.

FIELD OF THE INVENTION

The present invention relates to systems and methods for characterizing and quantifying a dispersive medium; specifically, measuring the concentration of particles or the tendency toward forming a dispersed phase within a fluid sample. The present invention also provides a program which uses these measurements of concentration to monitor and control operation of a process unit in a refinery.

BACKGROUND OF THE INVENTION

Thermal conversion is a process in which, by the application of heat, large hydrocarbon molecules are broken into smaller molecules with a lower boiling point. These operations are carried out in the industry of crude oil refining by plants such as a visbreaker, coker, and hydrocracker for obtaining intermediate or light cuts of higher value, from heavy residues of lower commercial value. As is evidenced by EP Pat. No. 768363, the term "process unit" can also be used in the place of "plant". The thermal cracking applied in the visbreaker process will also reduce the viscosity and pour point of the heavy residues.

It is well known that the fouling potential of a fluid can be estimated and characterized by the concentration of the dispersed phase, particularly by the concentration of the dispersed phase present in a specific size range. In hydrocarbon systems in particular, it has been recognized that the concentration of asphaltenes (i.e., carbon particles or opaque species) with linear dimension greater than about 2 microns in visbroken tars is a good indication of the fouling potential of the material.

The VSB process was developed some years ago with the intention of obtaining a viscosity decrease in heavy products in order to reduce the amount of higher valued flux to meet the viscosity specification of the finished heavy fuel product. Today, however, it is managed with substantially different objects, namely with the aim of obtaining a maximum transformation into middle and light distillates to meet the market requirements.

The controlling factor in obtaining a high conversion is the need to obtain a stable residue. In fact an increase of the cracking temperature certainly would involve a higher conversion in light and middle distillates, but it would produce a much more instable tar which would produce a final product outside the required stability specifications.

An increase of the light streams is achieved by increasing the cracking severity through an increase of the outlet furnace temperature of the Visbreaker furnace. While increasing this temperature arbitrarily will serve to drive the conversion rate higher, it also comes at the cost of producing a highly unstable tar as a precipitate in the process, with a high concentration of asphaltene particulates. This particulate matter constitutes a severe fouling threat to the energy recovery devices (i.e., furnace and heat exchangers) in the process. As such, in order to maximize the profitability a Visbreaker unit, it is desirable to optimize the outlet furnace temperature while maintaining the stability of the produced tar. While it is known that high temperature dispersants and anti-foulants can be introduced into the system to reduce the tendency and rate of fouling, prior art systems have not been entirely satisfactory in providing an automated system for determining an optimum type and/or quantity of chemical dispersants and anti-foulants to be introduced into the visbreaker unit in order to maximize plant profitability. The present teachings will show that if the fouling potential of the tar can be quantified, then the precise level of chemical inhibitor can be dosed to maximize the plant profitability.

It is also known that the fouling tendency of a hydrocarbon feedstock, or blends thereof, can be related to the tendency for insoluble organic materials to precipitate in heat transfer equipment, or other equipment for a refinery process unit.

Therefore, in one aspect the present invention provides a simplified, automated system and method that can easily be used to carry out optical analysis of visbroken tars and other fluid samples in order to characterize and quantify the concentration of particles within the fluid sample with high accuracy and reproducibility. In another aspect, the present invention utilizes these concentration measurements to determine the fouling potential of the visbroken tars, and regulates the introduction of chemical inhibitors into the visbreaker unit to improve the yield of light streams. In yet another or further aspect, a sequence of aliquots are prepared from the same sample at different dilutions to drive phase separation, producing a sequence of concentration measurements correlated to a classical measurement of peptization value (PV), a qualitative measure of the product quality. In yet another or further aspect, this invention utilizes concentration data to estimate the fouling potential of a feedstock, relates the concentration data to the fouling potential of the feedstock, and provides optimal dosage of chemical treatment to reduce the rate of fouling. These and other aspects of the present invention will become apparent to those skilled in the art upon review of the following disclosure.

SUMMARY OF THE INVENTION

In one aspect, the present invention provides a system and method for estimating a concentration of inhomogeneities contained within a tar byproduct of visbreaker operations. The invention does so by measuring the modulation of transmitted light through a fluid sample. The system uses a strongly convergent optical lens system to focus light onto a prepared sample. In one exemplary embodiment, the optics of a conventional optical microscope are used. A 3-dimensional translation stage is installed downstream of the focusing optics so that the sample can be scanned over a large region, and at a specific focal plane. A photo detector is placed on the opposite side of the stage from the focusing optics to measure the transmitted light through the sample. The photodetector is read-out by an analog-to-digital converter (ADC) in order to provide a digital (i.e., quantitative) measure of the transmitted light intensity. The translation stages are then moved in a pattern, such that the intensity of the transmitted light is measured over a representative path across the sample. When an opacity, scatterer or opaque particle of a threshold size is encountered in the sample, the intensity of the transmitted light is strongly attenuated. Such change of light intensity is then correlated with the detection of an opaque particle in order to characterize and quantify the concentration of particles within the fluid sample with high accuracy and reproducibility. Data processing algorithms are implemented to determine the background noise level associated with the acquired data and to set a threshold level. As such, a specific signal-to-noise ratio can be specified to define when a detection event is registered. Size discrimination may be achieved according to the physical dimensions of the beam waist of the focused light beam.

In another aspect, the present invention utilizes the concentration measurement data to estimate the fouling potential of visbroken tars in a visbreaker unit in order to regulate introduction of chemical inhibitors into the visbreaker unit and improve the yield of light streams. The invention provides an automated program which allows the user to maximize the production of light streams by modeling the correlation between operational parameters such as feed quality, cracking severity, conversion rate, run length, and fouling rate of the subject exchanger or furnace in order to regulate introduction of chemical inhibitors into the visbreaker unit in accordance with customer specifications and/or production requirements.

In another aspect, the present invention utilizes a method for controlling and optimizing chemical injection into a process unit to control fouling. The method uses an optical device to measure the fouling propensity of the process fluid at various points within the process unit. The measurements are compared with one another and prediction methods are used to evaluate the fouling potential within the unit, and determine the proper chemical dosage. Antifoulant chemical is then introduced into the unit to control the rate of fouling. The method and application continue on a frequent basis to maintain optimal fouling control within the unit.

BRIEF DESCRIPTION OF THE DRAWINGS

FIG. 20 is a table illustrating VFM particle count data for a particularly asphaltenic crude oil (Crude A) blended at several ratios with a standard crude slate (Crude B);

FIG. 21 is a graph illustrating VFM particle count data for a particularly asphaltenic crude oil (Crude A) blended at several ratios with a standard crude slate (Crude B);

FIG. 22 is a graph illustration actual furnace inlet temperature declines due to fouling as measured in the field;

DETAILED DESCRIPTION OF THE INVENTION

Figure 1:
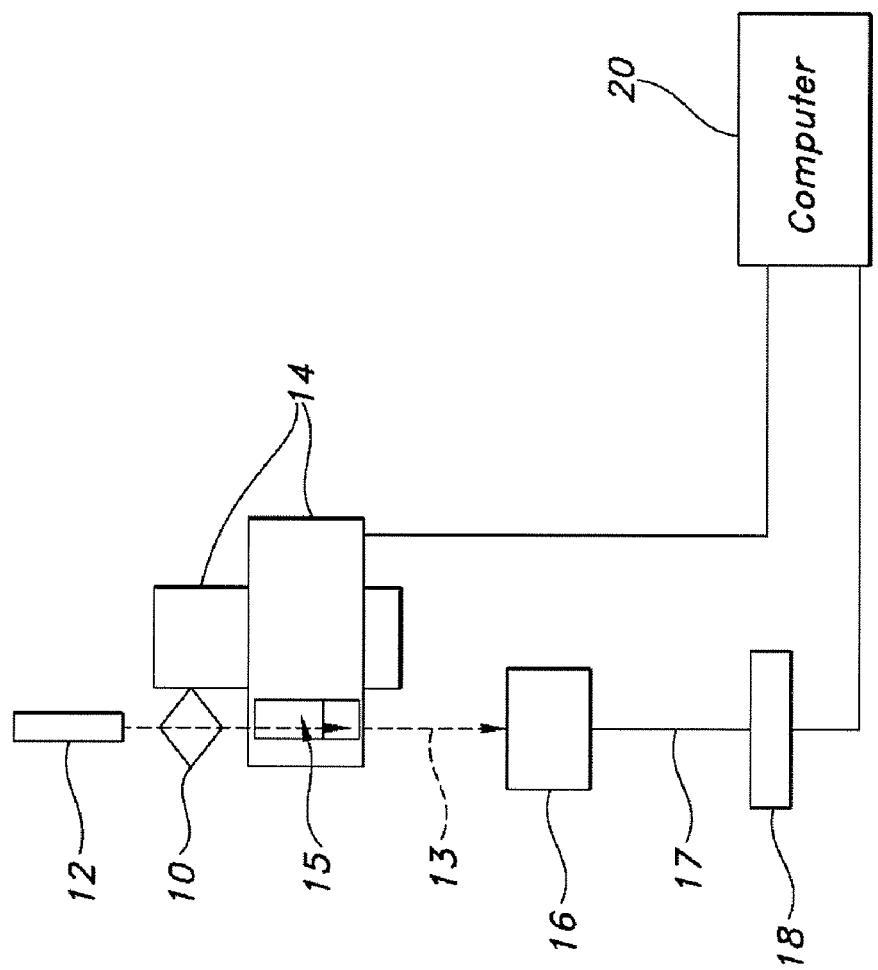
FIG. 1 is a view of the scanning apparatus of the present invention, showing the schematic relationship of the various elements.

Exemplary embodiments and examples describing the present invention will be described below with reference to the accompanying drawings. As shown in FIG. 1, this invention uses an optical system as generally indicated by the number 10, which in the present exemplary embodiment comprises a convergent lens, a light source 12, and a multi-axis translation stage 14. The light source 12 may be implemented, for example, in the form of a solid state visible laser. An infra-red (IR) laser may also be used, and is in some cases preferable owing to the fact that HC solutions are typically much more transparent to IR light, than visible light. The translation stage 14 may be moved horizontally in the x and y directions in response to control signals generated by an associated computer 20 to direct the light beam along a plurality of paths through the sample. The third axis moves the stage vertically, towards and away from the focusing lens. This permits selection of a focal plane within the sample. In another exemplary embodiment, the present invention contemplates providing means for moving the light source 12 with respect to the sample, thereby allowing the light beam to be directed through the sample to achieve the same results. Moreover, the present invention also contemplates usage of a flow cell to receive a flow of sample fluid, wherein the sample fluid flows through the flow cell while the light beam is directed through a portion of the flowing sample. Also implemented is a photodetector 16, for example, a PIN photodiode, located on the opposite side of the stage 14 to detect light 13 being transmitted through the sample volume, which is located on the translation stage. The photodetector 16, in turn, is connected by a connector and cable 17, for example, a twisted pair with BNC connector, to an analog-to-digital (A/D) converter 18 to quantify the transmitted light intensity. As described below, this is done to sample or detect the occurrence of inhomogeneities in light transmission which may be caused by mineral and other inclusions, and agglomerating or stable localized dark matter of various types.

In one exemplary embodiment of the invention, a colloidal fluid sample material of thick viscous tar sampled from a Visbreaker is placed on the translation stage 14. Depending on the conditions in the Visbreaker unit, the sample may or may not contain asphaltene (or carbon based) particles. The asphaltene particles within the tar medium are opaque to visible light. The tar medium is also opaque to visible light when the path length through the medium typically exceeds a linear dimension of about 1 cm. A sample volume is dispensed on a slide, or flow cell 15 such that a typical sample thickness of 10-20 microns is produced. As such, the thickness of sample medium should be made thin enough so as to provide a differential transparency between the viscous tar medium and the asphaltene particles in question. In this exemplary embodiment, in order to optimize light transmission from a low power light source, a solid state laser that produces radiation at about 633 nm is chosen. This provides adequate power at a suitable region in the EM (electromagnetic) spectrum to provide transmission through a thin layer of tar, while the carbide particles remain opaque.

Figure 3:
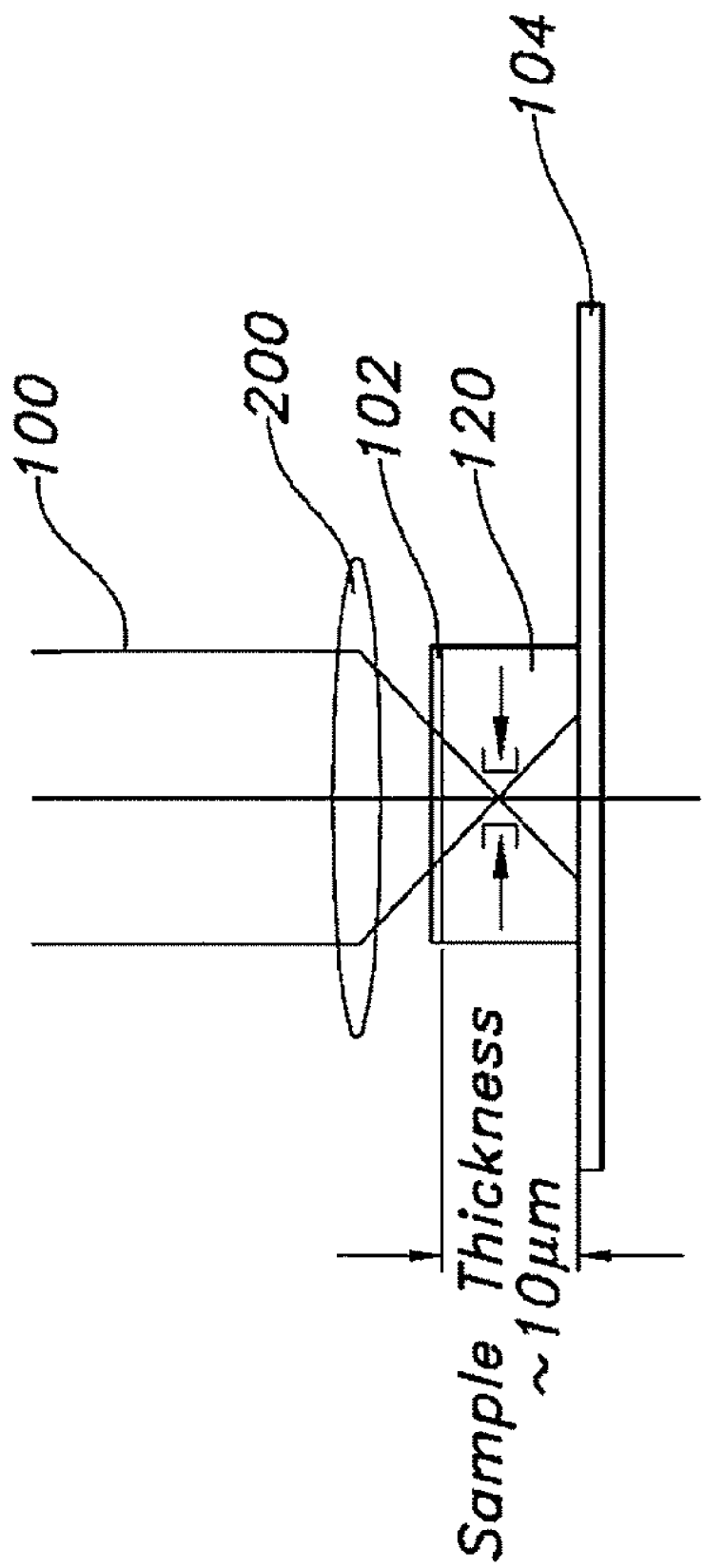
FIG. 3 is a diagram illustrating optics used to convergently focus a light beam to a narrow beam waist.

In order to have sensitivity to the specific sized inhomogeneities, appropriate optics should be used to focus the laser light onto the sample. The choice of a monochromatic light source allows the design of the optics to be optimized. As shown in FIG. 3, a highly convergent lens system 200 is used to focus the light beam 100 down to a beam waist of approximately 1 micron. The size of the beam waist determines the minimum cross-dimension an inhomogeneity must have to fully attenuate the laser light. If an inhomogeneity is smaller than 1 micron, it will still allow the transmission of light. As such, the focusing optics define, in part, a threshold size for inhomogeneity detection. An equation for calculating the beam waist is as follows:

$$W = 0.61 \lambda / d$$

Where
W=beam waist (1/e) width
λ=wavelength of light
d=numerical aperture

For example, if λ=633 nm and d=0.56, then W=0.7 μm. Since we are interested in inhomogeneities larger than 1 micron (and smaller than ~20 microns), we do not use an IR laser, even though the HC solutions are more transparent to IR radiation because the beam waist would increase in size for the given optics. As such, we would reduce the sensitivity of the instrument. Preferably, the wavelength and beam waist are also chosen to minimize interference artifacts that may arise as the concentration of dispersed phase increases or the sample thickness varies (e.g., under a cover slide.)

The fluid sample 120 thickness is chosen to be about 10 microns. The beam 100 is focused on the slide 104, below a cover slip 102, or a flow cell in the sample volume. The depth and width of focus are constrained by the optical system and the selected light wavelength. In one exemplary embodiment, both dimensions are selected to be approximately 1 micron.

Figure 2:
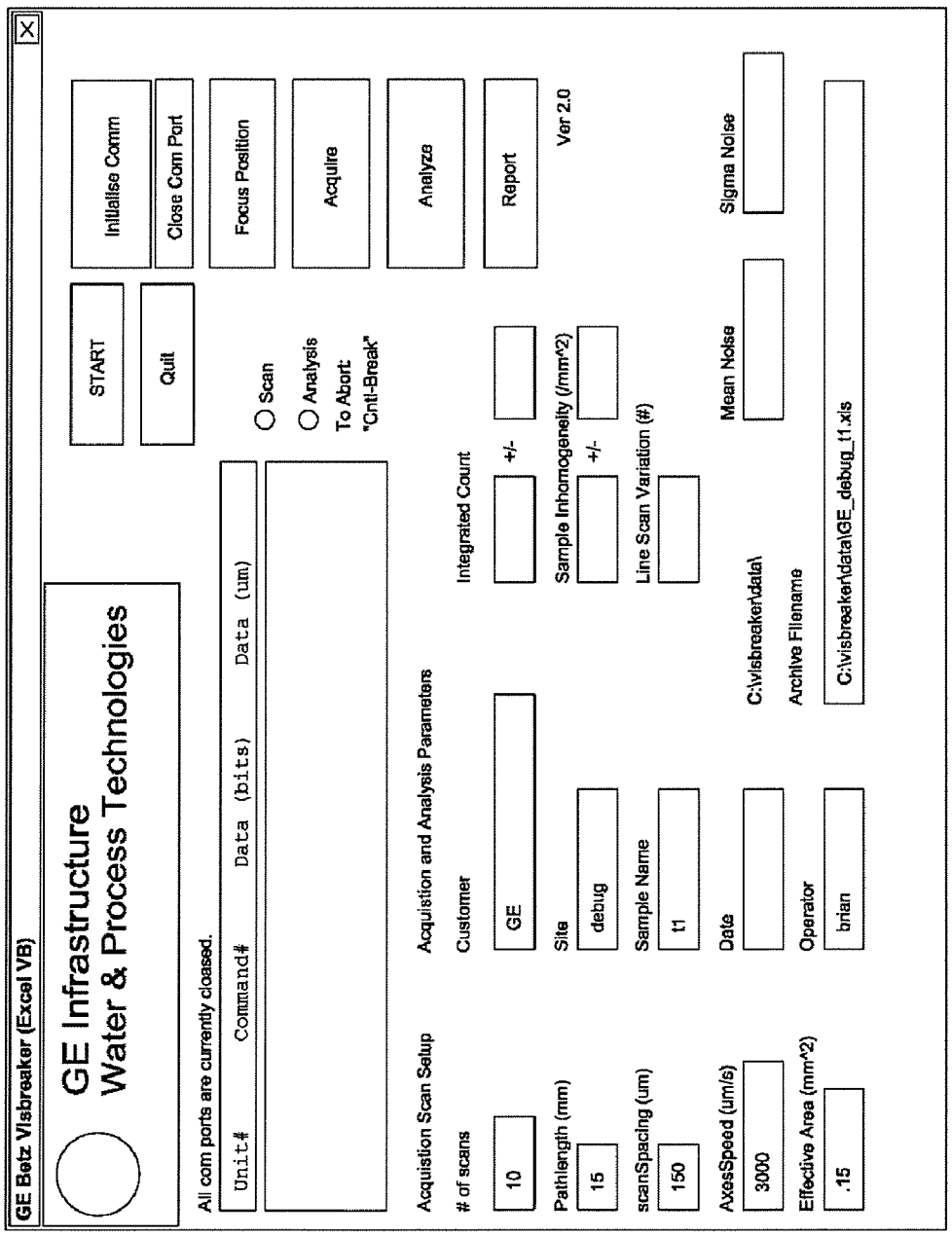
FIG. 2 illustrates an example of a computer screen displaying a data acquisition interface in accordance with the present invention.

FIG. 2 illustrates an example of a screen display presented by the software of the present invention. The screen display illustrated in FIG. 2 represents a data acquisition interface allowing the operator to specify a variety of scanning acquisition, analysis parameters, operating conditions of the instrument, and results of the measurement. The methods by which the operator selects items, inputs data, and otherwise interacts with the data acquisition interface are conventional, and further discussions of these operations are not provided herein. In an exemplary embodiment of the invention, data acquisition software was implemented via Visual Basic® in Excel® with analysis and signal processing code being implemented in GNU Octave, although those skilled in the art of software programming will appreciate that many other software programming means may be used to achieve the same results.

A testing plan was designed and implemented to validate and measure the scanning performance of an exemplary embodiment of the present invention. In particular, measurement repeatability is validated by analyzing the variation between identical measurements. Reproducibility of the data is examined by analyzing the effects of scanning different regions in the sample. This is complicated by the effects of sample inhomogeneity. Accuracy of the system is tested by comparing the scanning data with visual images and PV (PV=peptization value) of the sample. Precision of results is analyzed for statistical uncertainty with path length and by optimizing sample area, as discussed in more detail below.

Figure 4:
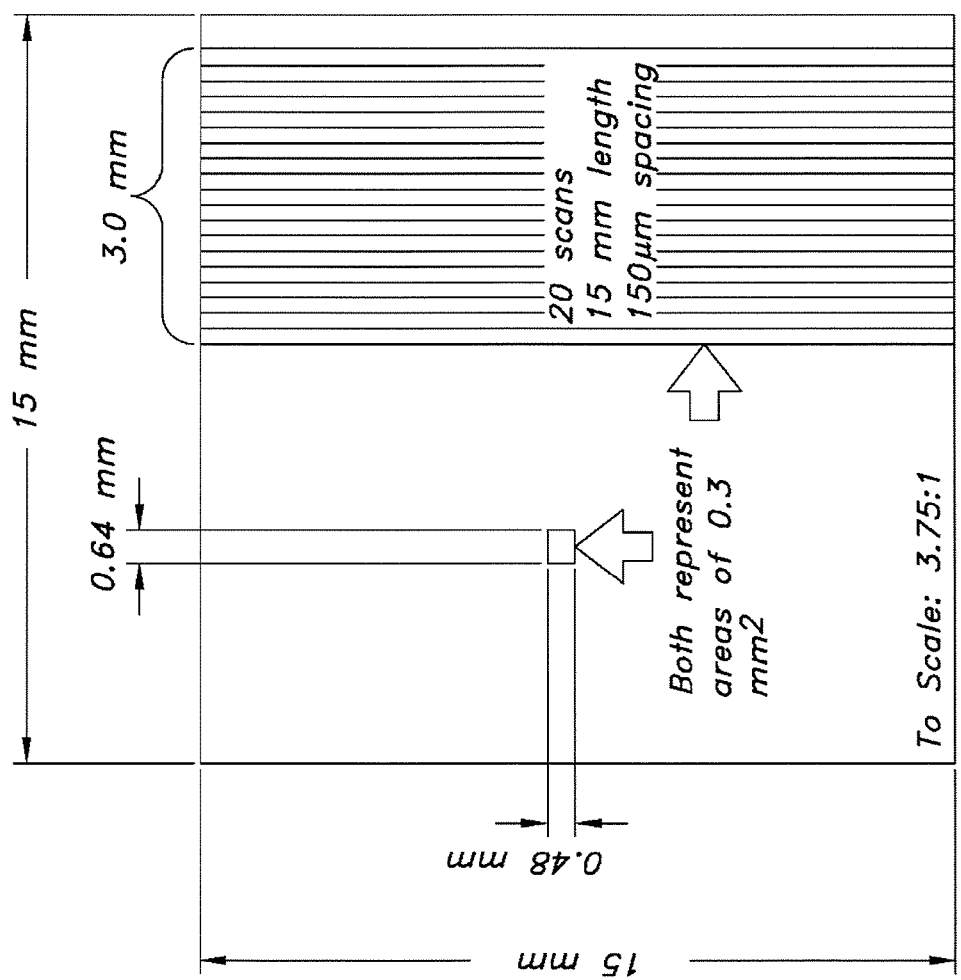
FIG. 4 illustrates a plurality of spaced apart linear scans compared with a solid block representing an equivalent effective surface area.

FIG. 4 illustrates an example of how the scanning system samples a large region of the sample. The array of linear scans (shown on the right side of FIG. 4) represent the same effective surface area as the small box illustrated on the left side of FIG. 4. For example, an array of 20 linear scans of 15 mm length with a 1 micron wide laser beam effectively samples the same area as does the smaller 0.48 mm×0.64 mm box. However, by arranging the sampling path to extend over a larger region of the sample, the effects of sample inhomogeneity, local fluctuations in the sample, and sample variation are reduced drastically. As such, the statistical results are much more accurate and reproducible.

To demonstrate the repeatability of our scanning results, five identical 15 mm scans from a same sample, each covering a 0.015 mm² effective area were measured. The measurement showed that the number of counts per 15 mm line scan were identical within 95% confidence limits. Increasing the sampling region to 20-15 mm scan paths, the same systematic effects were seen. After applying statistical analysis to the results, it was observed that the single line scan measurements are normally distributed, with a standard deviation (σ)=1.6 counts on a mean of 8.0 counts. Furthermore, the total integral count of the sample was 159 with a standard deviation of 9 counts. This shows that both the mean inhomogeneity count per path, and the total integral inhomogeneity count were statistically identical and repeatable, over the separate trials, thus demonstrating that instrument stability and repeatability is excellent. It also demonstrates that the fractional error can be reduced by increasing the sampling length. This is due to the fact that independent errors do not add linearly, but in quadrature.

As can be noted from the above data, the system of the present invention is capable of minimizing and quantifying the effects of sample inhomogeneity.

Figure 5:
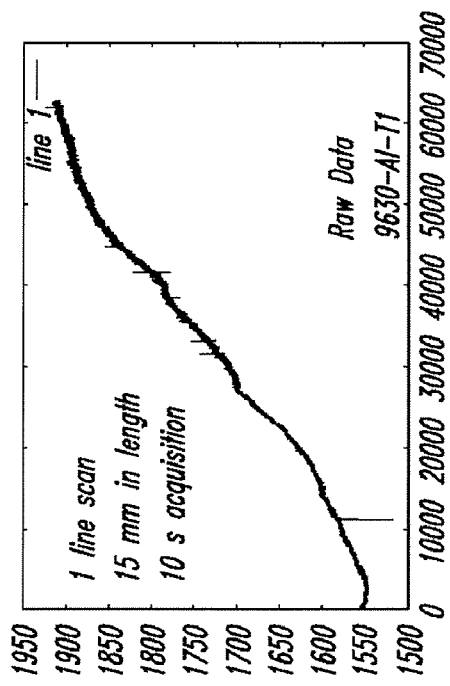
FIG. 5 is a graph illustrating raw light transmission data obtained over a single line scan.

Turning now to FIG. 5, there is shown a graph representing exemplary raw data obtained from a single line scan of 15 mm length taken during a 10 second acquisition window.

Figure 6:
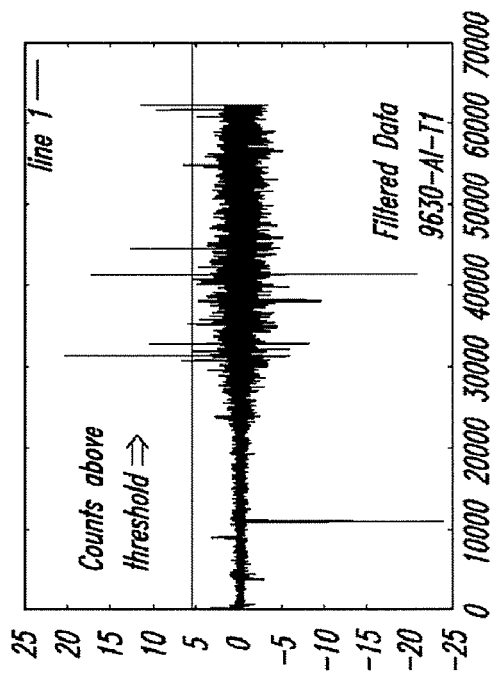
FIG. 6 is a graph illustrating the raw data of FIG. 5 after the data has been filtered to remove line noise and gross intensity variations.

In FIG. 6, the raw data of FIG. 5 is processed by a Fourier filtering to remove 50/60 Hz line noise and a median filter is used to remove gross intensity variations to extract the number of counts above a threshold value. This process may be repeated for all line scans (e.g., 20 line scans) to calculate the total homogeneity areal density of the sample under test. In one example, the number of peak counts from a single line scan is calculated as $$\rho_1 = (9 \pm 3) \div (15 \text{ mm} \times 1 \text{ } \mu\text{m}) = 600 \pm 200 \text{ mm}^{-2}$$

Repeating this calculation for a measurement spanning over 20 paths, the error decreases as shown below:

$$\rho_{tot} = (149 \pm 12) \div (20 \times 15 \text{ mm} \times 1 \text{ } \mu\text{m}) = 497 \pm 40 \text{ mm}^2$$

We see that the error decreases according to Gaussian statistics where the error propagates in quadrature which is a well known statistical property.

Figure 7:
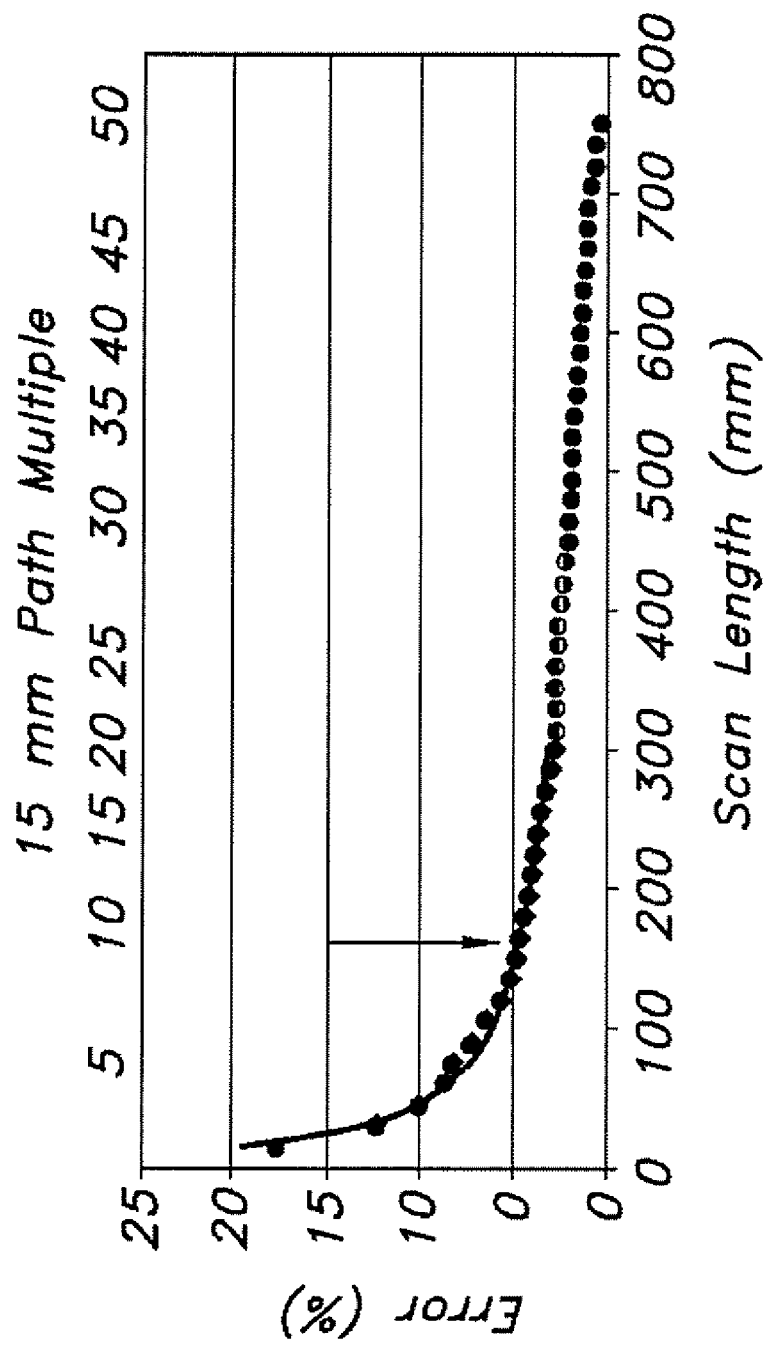
FIG. 7 is a graph illustrating decreasing statistical error as a function of overall scan length.

As shown in FIG. 7, an approximate 5% uncertainty is achieved at 10 line scans of 15 mm length (i.e., 0.15 mm² effective area). Statistical error is thus shown to decrease with $N^{-0.6}$, where N is the number of 15 mm path length multiples.

From the exemplary data of FIG. 7, it is shown that an overall path length of about 150 mm (10×15 mm) would achieve an approximate 5% error.

In order to determine the background noise in the signal as in FIGS. 5 and 6, the present invention provides a software algorithm, which automatically computes the background noise and sets a discriminator level or threshold for registering a sample inhomogeneity. A measurement of the light transmission is made when no scanning is occurring. Thus, the signal is an estimate of the nominal noise. Calculating the standard deviation of this signal distribution allows the estimate. The value can be used to determine a fixed signal-to-noise ratio on which to accept inhomogeneities.

In accordance with the present invention, the instrument is capable of quantifying the inhomogeneity of a solution in an automated and timely fashion.

To demonstrate the capabilities of the present invention, the following sample specimens, with various concentrations of asphaltenes were used for analysis and validation:

Specimen A: 9630 Asls, PV=1.7, low particulate density (highly diluted).
Specimen B: 9630-6, PV=1.4, intermediate particulate density (partially diluted).
Specimen C: 9630-7, PV<1.0, high particulate density, heavily cracked sample (slightly diluted).
Specimen D: 9630-mod, 13% 9630-7+9630 Asls, PV=about 1.35 (partially diluted).

Figure 8:
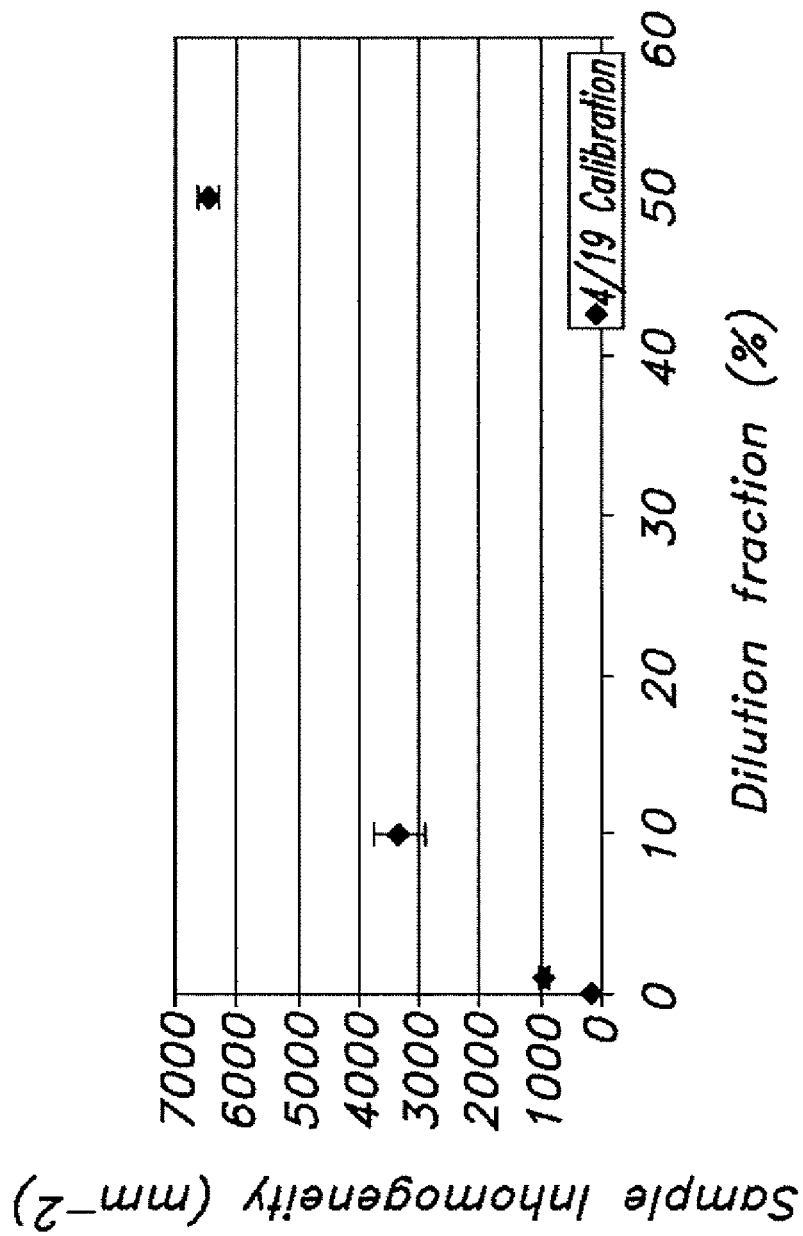
FIG. 8 is a graph showing the correlation of sample inhomogeneity, as measured by the instrument to samples with a varying degree of dilution from a fully cracked (i.e., high asphaltene particle density) sample.

The scanning results from these samples were then compared to photographs of the samples, and a correlation was found between the images and the scanned results. A graph showing the correlation of particle density as measured by the instrument to samples with a varying degree of dilution from a fully cracked (i.e., high asphaltene density) is shown in FIG. 8.

Overall, the testing results demonstrate that the system of the present invention provides good repeatability and shows correlation with visual image views. It has been shown that a relatively large sample area may be covered with automated operation, thus reducing the effects of local fluctuations in inhomogeneity density. Data can also be assigned an error to quantify precision of results.

We also disclose a program to monitor and control the operation of a Visbreaker unit in a hydrocarbon processing facility (refinery). The program allows the user to maximize the production of light streams (i.e., usually diesel) while maintaining a highly stable residual tar and reducing the chance that rundown of the tar will foul the preheat heat exchangers.

It is known that the stability of residual visbroken tar and its fouling potential can be measured by the peptization value (PV) and the hot filterable solids (HFT). Note that HFT and PV are two different metrics as HFT is a product specification whereas PV is a characterization of the visbroken tars towards the asphaltene precipitation potential. The optical measurement device (referred to hereinafter as 'VFM') of the present invention measures a quantity which is a measure of the opaque filterable solids within a tar sample. The automated program of the present invention utilizes the VFM concentration measurement data to estimate the fouling potential of the visbroken tars. This estimate in turn is used to gauge the needs for optimum feed of chemical treatments.

It is known that high temperature dispersants and anti-foulants are the main components in a chemical regiment used to treat Visbreakers. There are specific chemical families that are particularly effective for use in the Visbreaker for reducing fouling of heat exchanging surfaces (i.e., exchanger, furnace, etc.) and subsequently stabilizing the produced visbroken tar. The program of the present invention is configured to select the type and quantity of chemistry required to satisfy production requirements. Specific chemical entities include, but are not limited to polyisobutenylphosphonic acids and esters, polyisobutenylthiophosphonic acids and esters, alkylphosphonate phenate sulfides and disulfides that may be neutralized with alkaline earth metals or amines polyisobutenyl succinimides, polyisobutenylsuccinate alkyl esters, magnesium or calcium salts of alkyl or dialkylnaphthelene sulfonic acids as described in U.S. Pat. No. 4,927,519 and EP Patent No. 321424B1.

These antifoulant materials have been found to function at low dosages, 1-200 ppm, to prevent the undesirable deposition or fouling of surfaces in visbreakers, as well as prevent the carboneceous deposition in visbroken heavy oil products (tar). Fouling in heat exchangers is most generally thought to occur by first generating an unstabilized macromolecular particle that is no longer dissolved in the fluid, or is no longer a stable colloidal species. This occurs due to the thermal stress on the hydrocarbon. Initial deposition occurs, and further destabilized species adsorb onto the site of original deposition. Bigger particles in the hydrocarbon will be more prone to contact and coalesce to the surface. Dehydrogenation of the adsorbed hydrocarbon will be driven by heat and make the deposit more tenacious as crosslinking reactions occur.

Figure 9:
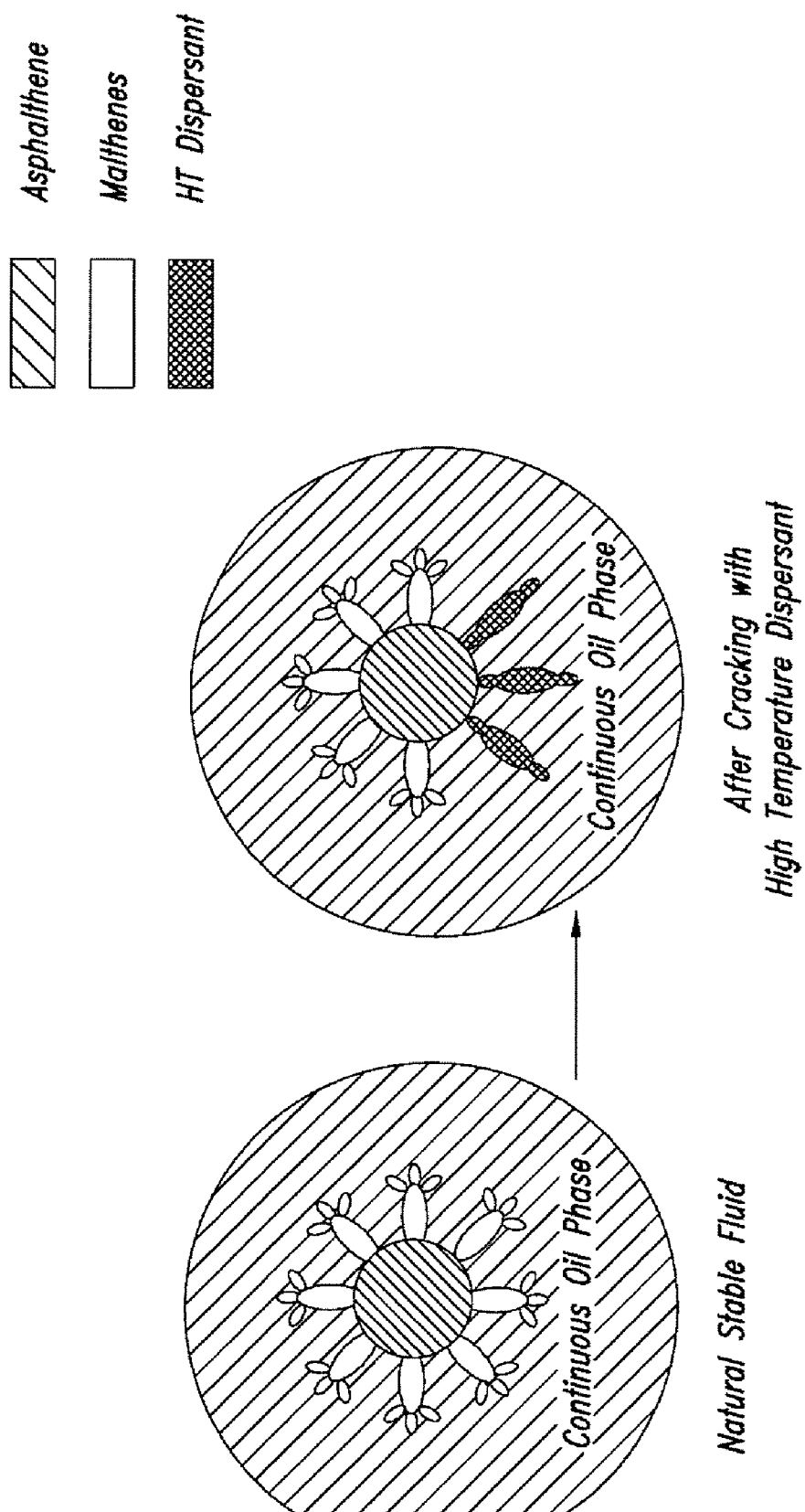
FIG. 9 is a schematic of the mechanics of the chemical effect of the dispersants.

The dispersants are generally understood to function by a variety of mechanisms. First, the dispersant materials adsorb to the surfaces of growing insoluble particles and act to keep these particles small; typically less than 1 micron. Thus, the particles are more prone to continue to flow through the system and not settle on heat exchanger or other surfaces. This can be described by Stokes law, which is dependent on the radius of the particles. This is schematically shown in FIG. 9. The dispersants act by a combination of steric stabilization, which acts to repel approaching particles (dramatically increase entropy of local system and drive solvent in between particles), and blocking of polar sites on the particles which act as a driving force for coalescence. Light scattering evidence exists that shows that dispersant treated thermally stressed fluids generate particles that are up to two orders of magnitude smaller than untreated hydrocarbon fluids.

Even if the particles are not small, the above mechanism explains how the particles will be less prone to coalesce to other particles in solution, or to material already deposited on the surface.

It has also been shown that the nature of the surface plays a role in the ability of thermally stressed fluids to deposit. Metal surfaces with higher roughness, edges, or polarity are more prone to fouling. These dispersants will adsorb to such surfaces and discourage particulate or amorphous insoluble hydrocarbon from sticking to the surface.

The reaction of hydrocarbons at elevated temperatures with oxygen (even very low levels such as <5 ppm) will result in formation of polar functionalities that can drive coalescence of particulate, as well as accelerate the dehydrogenation of adsorbed hydrocarbon, which makes its removal from the surface by turbulent flow much less likely. Dispersant adsorption will block the mass transfer of the oxygen to the surface, and some of these described anti-foulants have antioxidant abilities by interfering with radical reactions.

In addition, the visbroken tar is generally believed to be colloidal in nature, with more highly polar and higher molecular weight asphaltene species being stabilized in the fluid by smaller resin molecules. As the thermal stress disturbs the relationship of the adsorbed resins to asphaltenes, and by driving the conversion of resins to asphaltenes, and by making the asphaltenes more polar, these systems can be described as being more "unstable" or prone to deposition. The dispersants described here are believed to replace the disturbed or destroyed resins and re-stabilize the asphaltene system.

As described herein, the VFM measurement data gives information on the solids content in the residue (tar). Higher amounts of solids will give a higher precipitation potential. The solids might be introduced into the system by the feed (poor feed quality) and/or through the cracking process. The higher the cracking severity the higher the solids content in the residue likely will be.

Based on defining a baseline, which is unit dependent, the VFM data provides information in increasing response to decreasing solids content in the tar. Depending on the main cause of the solids increase (feed or cracking severity) the device can help to optimize the chemical injection rate (if solids are from feed or severity want to be maintained) in order to maintain the fouling rate and thus keeping unit runlength under control. If solids increase is due to cracking severity only, the VFM measurement provides an early warning to potential instability of the tar and cracking severity can be reduced by decreasing the furnace outlet temperature (FOT).

Figure 10:
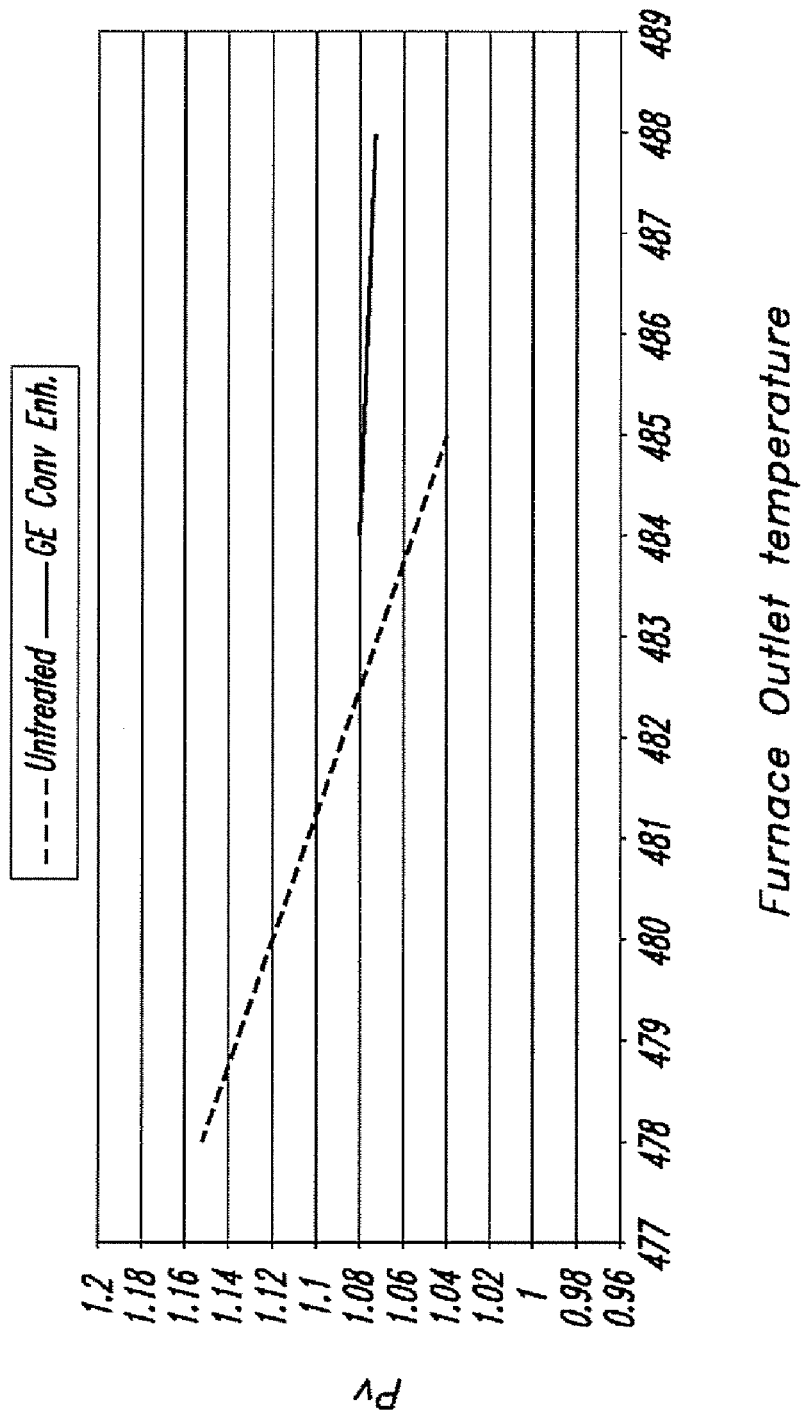
FIG. 10 is a graph of the relation of PV to the Furnace Outlet Temperature (FOT) with and without chemical treatment.

FIG. 10 shows a correlation of FOT versus PV. Increasing the FOT will reduce the PV value up to instability (i.e., PV=1.0). With the appropriate treatment, the PV will remain higher (i.e., stable) at the same temperature. Also note that the slope between the treated and untreated curves is different, with the treated curve having a much gentler slope. This provides more security and flexibility to the conversion enhancement objectives as the treatment acts as a buffer to the rate of PV change with FOT. Accordingly, FIG. 10 is the correlation of the Furnace Outlet Temperature versus Pv showing that by increasing FOT the Pv will reduce up to instability, and with treatment, the Pv will be higher at the same temperature, but also the slope is different indicating that we provide more security and flexibility to the conversion enhancement objectives. By comparison, other known treatment systems, such as those described in European Patent Nos. 0321424 B1 and 0529397 B1 to Faina, et al., do not impact Pv in the manner described by the present invention.

Comparing the difference in the VFM measurements from the tar in the inlet of the furnace to measurements in the outlet of the furnace gives a direct measure of the severity of the cracking. When the VFM measures inhomogeneities in the outlet stream, action can be taken on the process side, specific to customer specifications. For example, the simplest action to be implemented is reducing the cracking severity in order to reduce the fouling rate on the furnace, exchangers, columns bottoms or soaker drum. This reduces the risk and rate of fouling deposits, but it also reduces the amount of light hydrocarbon stream produced, so it reduces the profitability of operations. This course of action is accompanied with the feed of high temperature antifoulant chemistry at the rate of approximately 100 ppm. In order to maintain the highest efficiency of conversion and therefore the highest profitability, the goal is to increase the tar stability (increase the P-value) by replacing the converted resins by high temperature dispersant at a higher dose that is up to about 500 ppm of chemical is injected. The economical optimum to provide maximum profitability to the refinery is dependent on the individual refinery operations and objectives and is likely on the order of about 300 ppm. The specific value is determined with the use of the VFM measurements and our quantitative statistical models.

Our MRA models attempt to define a mathematical correlation between the operational parameters such as—feed quality, cracking severity, conversion and the fouling rate of the subject exchanger or furnace. By normalizing the mathematical model, the fouling rate is isolated from the varying operational parameters and the real fouling rate can be demonstrated and quantified. By developing a corrected model which reflects the residuals between the predicted model and the actual measured parameter, statistical process control techniques may be applied to quantify the performance of the chemicals applied to control fouling in the visbreaker unit. Precise determination of the fouling potential in this manner allows a refinery to start treating an opportunity crude and quickly reach an optimum set of operating conditions without incurring fouling, or to quickly change furnace conditions (i.e., temperature) in order to increase or decrease the amount of specific fractions in the product (i.e., distribution of components and/or composition of visbroken product) which may be required for immediate production needs, while assuring that operation remains within a safe stability band. In addition to enhanced yield or throughput, it provides enhanced flexibility with minimized risk.

The present invention is adapted to control chemical feed based on VFM measurements to maximize yield of light HC streams in Visbreaker operations. The VFM can also give an estimate of tar stability, which is proportional to HFT measurements. The program of the present invention controls chemical feed based on a predefined furnace outlet temperature, and uses predictive modeling to verify and predict performance based on VFM measurements. The chemical feed rate is then directly tied to customer driven performance measurements such as run length and/or conversion rate. High temperature dispersants can replace the converted resins to maintain tar stability while increasing the cracking severity; or, the system may increase tar stability by maintaining constant cracking severity. Moreover, measuring the tar characteristics with the VFM before and after the furnace indicates the amount of particulates produced directly in the cracking process.

A process for establishing effective visbreaker treatment may be summarized as follows. First, the user clearly defines the problem to be solved. Next, a unit survey or blank test of visbreaker operations is performed. Next, operational data obtained from the unit survey is analyzed, and baseline performance parameters are defined. Next, performance goals are measured in accordance with mutually agreed upon production goals and requirements, and then an appropriate treatment procedure may be designed. Next, the treatment procedure is implemented, monitored and serviced, and finally performance reports and quantity benefits may be provided.

Figure 11:
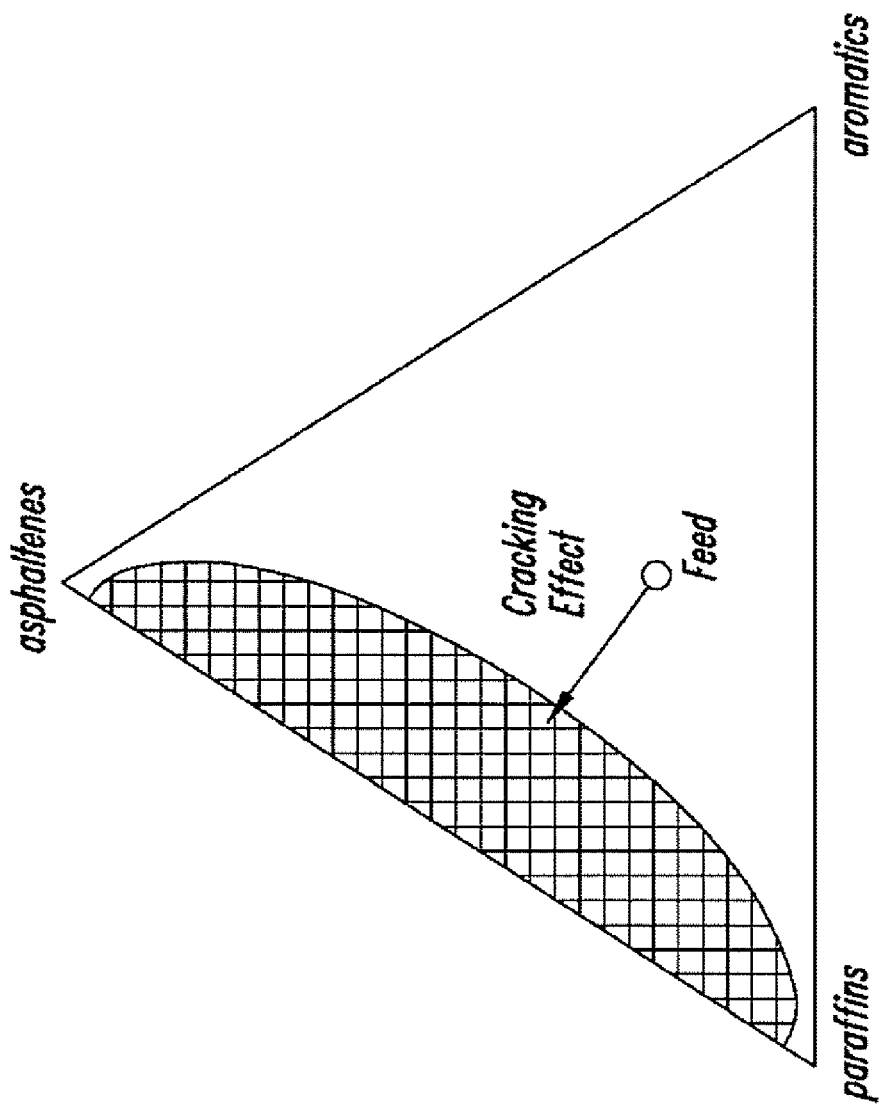
FIG. 11 illustrates tar stability and conversion as asphaltenes are disbursed in the continuous phase through the peptizing action of aromatics and resins.

As shown in FIG. 11, tar stability conversion occurs as asphaltenes are disbursed in the continuous phase through the peptizing action of aromatics and resins. It may also be noted from the illustration that cracking modifies the equilibrium so that asphaltenes could cause precipitation—low peptisation value.

Figure 12:
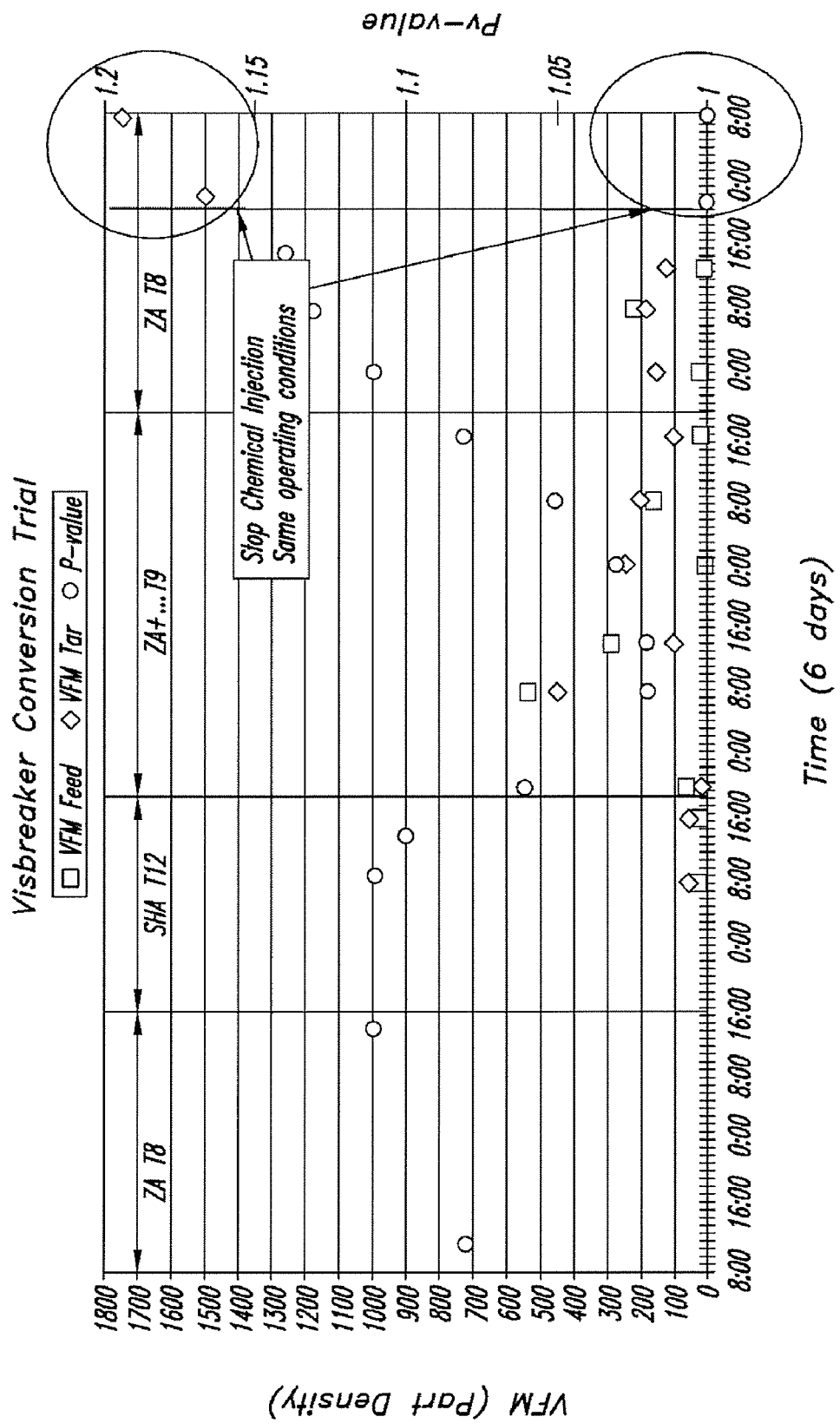
FIG. 12 is a graph illustrating raw data obtained from a visbreaker conversion trial.
Figure 13:
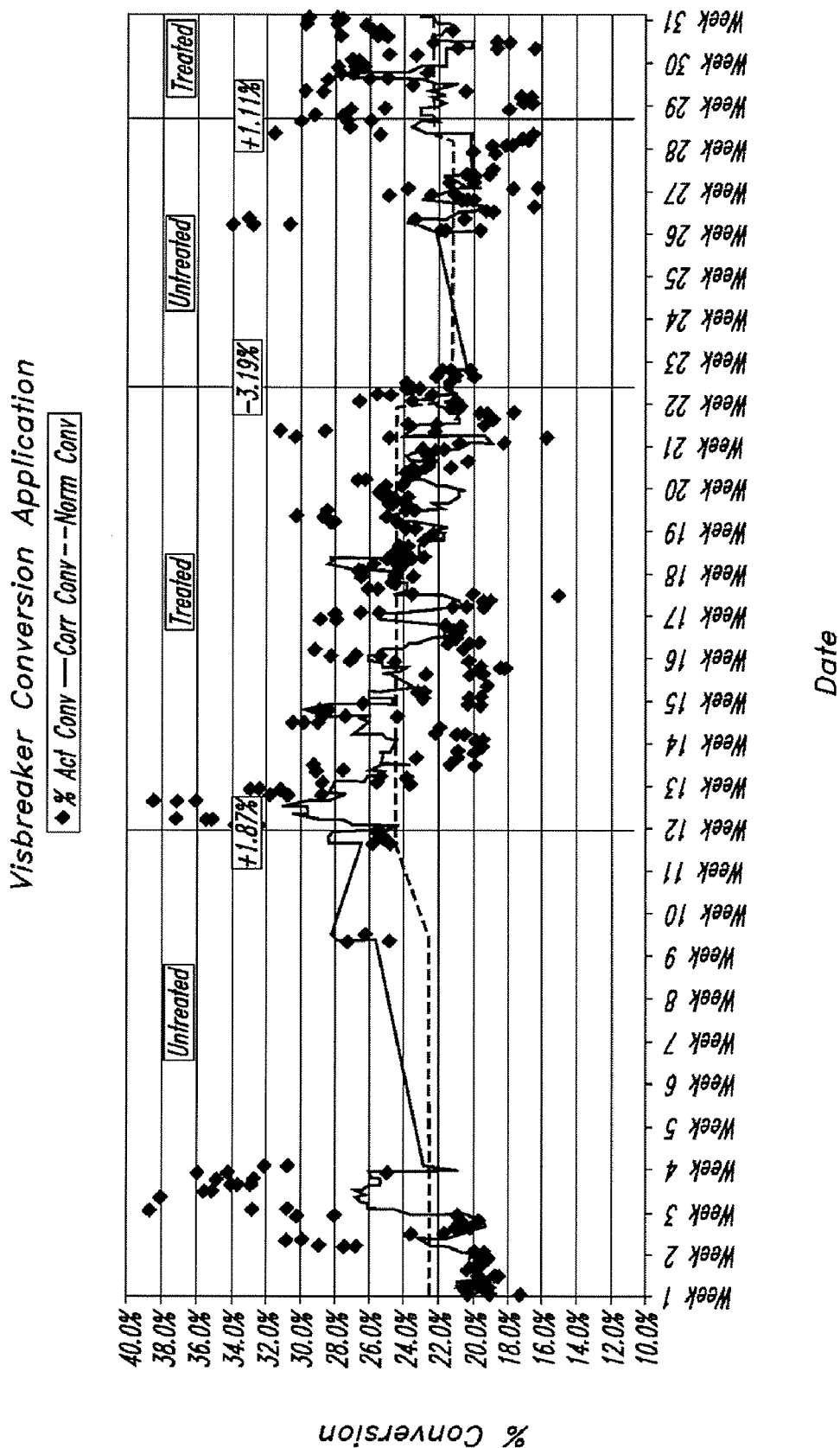
FIGS. 13-16 are graphs illustrating raw data obtained from a conversion enhancement application.
Figure 14B:
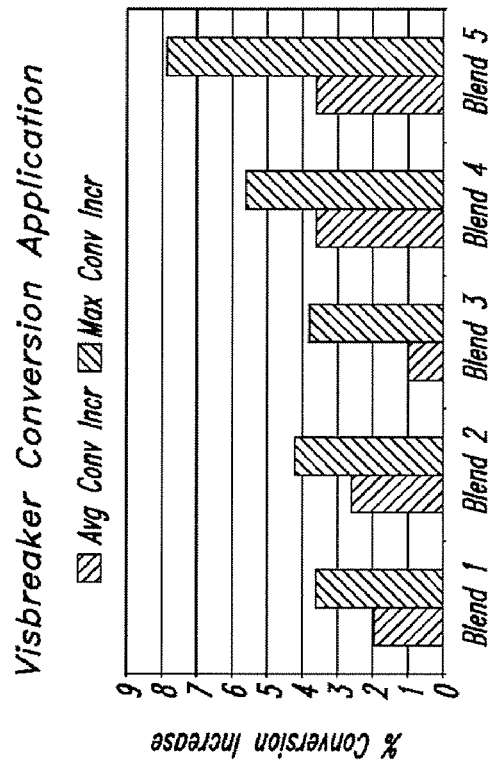
Figure 14A:
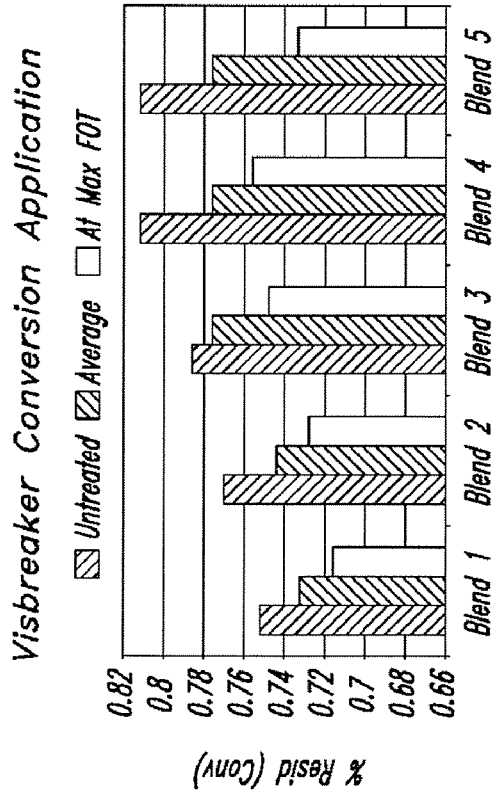

Exemplary data recorded from a visbreaker conversion trial is shown in FIG. 12. As it is noted from FIG. 12, the circled regions represent areas to stop chemical injection under the same operating conditions.

Figure 15:
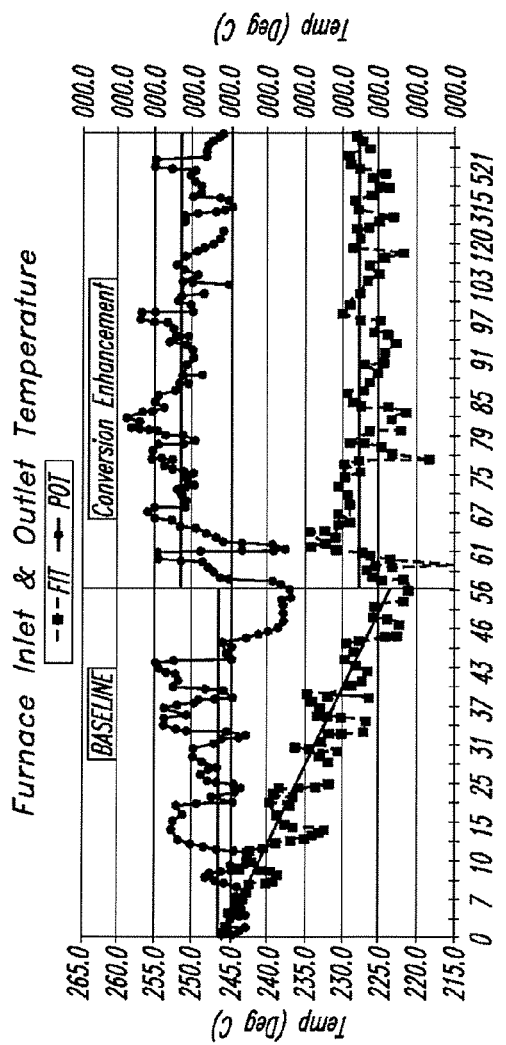
Figure 16:
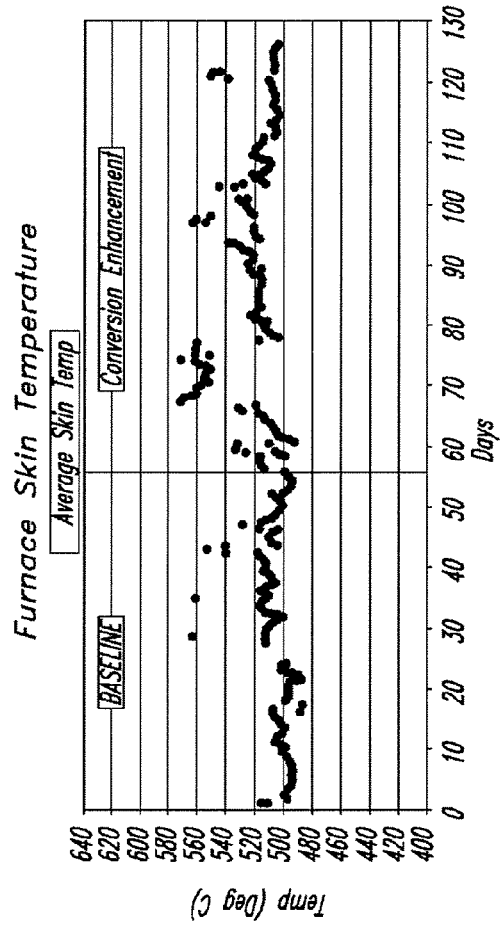

FIGS. 13-16 illustrate exemplary data obtained during conversion enhancement application. As it can be noted from the illustrated data, an overall +3% conversion increase was achieved. In FIG. 15, Thermoflo 7R630 was injected before preheat: average 300 ppm. It has to be noted that even a conversion increase by 1% in the treated charge has to be considered extremely satisfying in terms of profit.

Figure 17:
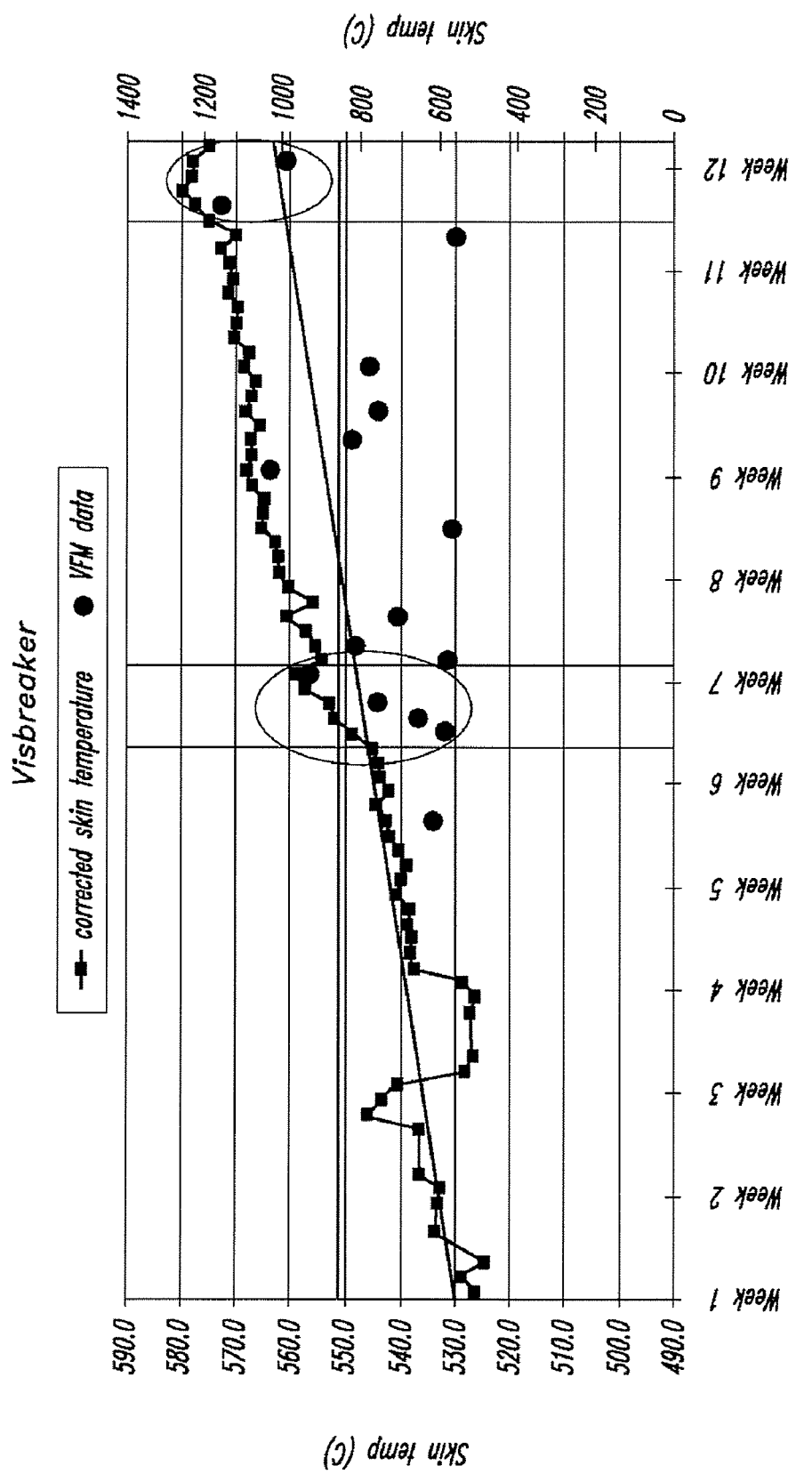
FIG. 17 is a graph illustrating VFM data versus corr. skin temperature.
Figure 18:
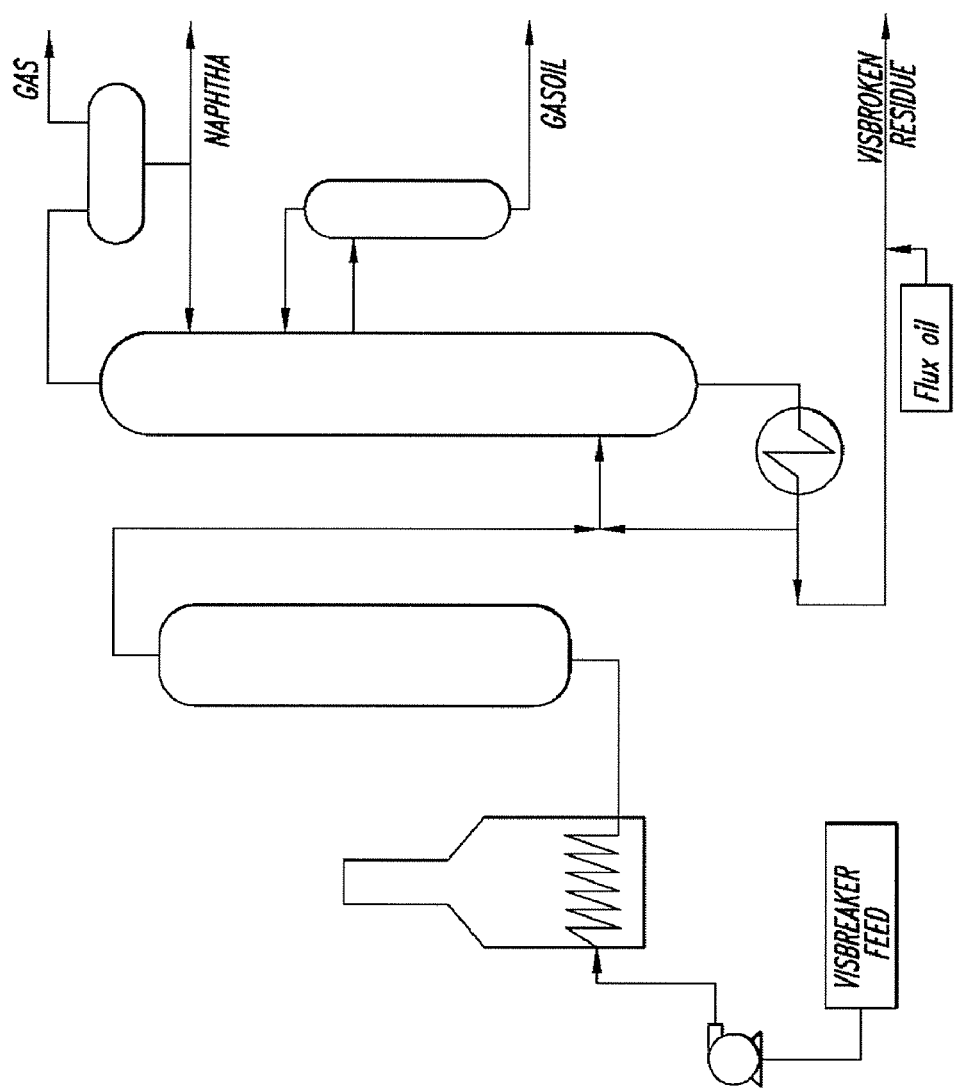
FIG. 18 is a schematic diagram illustrating exemplary visbreaker process types.

FIG. 17 illustrates VFM data versus corrected skin temperature over time, and FIG. 18 is a schematic diagram illustrating exemplary visbreaker process types.

The operation described above of path length sampling to develop a measure of concentration of dispersed phase correlates well with a conventional HFT measure of hot filtered tar and may also be used with a suitable protocol to derive the classical peptization value Pv. This allows the VFM to be used to assess the quality of the visbreaker product and efficiently blend or produce various required fuel or other oils. The classical procedure for measuring Pv, in use for decades, involves slowly adding graded amounts of pure n-cetane $C_{16}H_{34}$ to a sequence of samples of the product, maintaining each diluted sample in a heated bath for a time (e.g., thirty minutes) to allow the asphaltenes to agglomerate, and then detecting the concentration of tar. The different samples provide a graph of the product stability, with an abrupt increase in tar separation at the peptization value Pv. The concentration measured by the VFM of the present invention provides an effective tool for performing such a Pv measurement quickly and repeatably.

One suitable protocol substitute n-heptanes for cetane in the sample preparation procedure, allowing the dilutions, heating and settling to be performed quickly—on small samples, at lower temperature, and in shorter times. A classical P value is expressed as 1+Xmin, where Xmin is the maximum dilution before flocculation occurs expressed in number of milliliters of diluent n-cetane per gram of sample. For use with the VFM of the present invention, using n-heptane as the diluent, the sequence of samples with successively increasing dilution may be heated in a water bath at 100° C. for fifteen minutes, allowed to cool and stand for fifteen minutes, and then measured with the VFM. This substantially reduces the sample preparation time, and because the VFM requires only a small path sampling procedure, the entire array of samples may be placed on a single slide—for example, a 9-well microsample plate, for the concentration detection step, so measurement is simplified, and made quantifiable and repeatable. Because of the lower molecular weight of the lighter heptane diluent, a correction factor 1/0.443 is applied to the diluent volume Xmin to correct for the different molecular weight of cetane, so that the resulting P value is identical in value to the classical measurement. A series of samples can be placed on the stage. Each sample comprises a small amount of aliphatic hydrocarbon (i.e., n-cetane, n-heptane, etc.). The more aliphatic compound that needs to be added, the more stable the tar. The light transmission is then measured over a scan path on each individual sample. This allows a functional comparison to be made of optical density to the amount of aliphatic added to each sample.

Figures 19A, 19B:
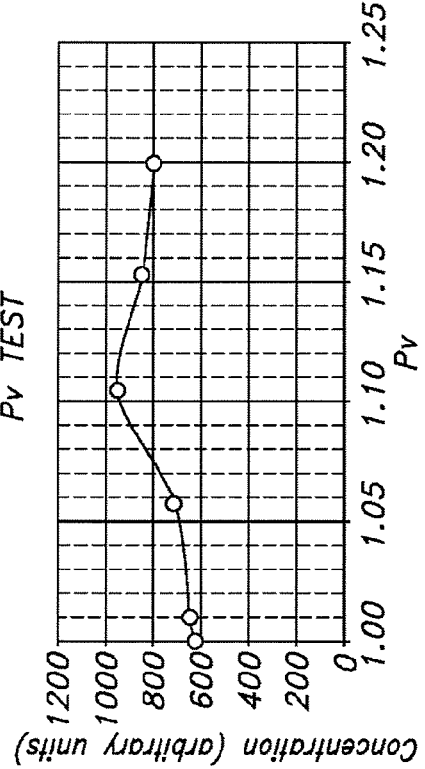
FIGS. 19A, 19B illustrate Pv measurement with a measurement system of the present invention.

FIG. 19A illustrates the derived Pv obtained by this procedure for five samples of visbreaker fluid, compared to the P values determined by the classical n-cetane laboratory testing analysis of the samples. The measurements are essentially identical. FIG. 19B graphs the VFM concentration measurement (in arbitrary units) illustrating the onset of instability and flocculation. The value Pv is readily visible as the point at which there is a rapid increase in sample opacity with a relatively small increase in the amount of the aliphatic (heptane) diluent. This abrupt change in the VFM concentration measurement among the tested samples, may be automatically defined as an output with a straightforward software comparison algorithm to provide this measurement of product quality or fluid stability. Other aspects of the sample preparation such as the preparation of a set of different dilutions and loading onto a microsample array for concentration measurement may be fully automated, using various injection, handling and transfer mechanisms that will be familiar from similar tasks performed by equipment used to automate the handling, processing and analysis of chemical, biological, medical or genetic sequencing materials.

Further, the program described above can be adapted to optimize the control of fouling in a heat exchanger network, or other equipment for a refinery process unit (such as a visbreaker unit, coker unit, hydrocracker unit, or crude unit), based on a-priori detection of particulate agglomeration, size distribution and insolubility. More specifically, fouling caused by asphaltenic instability due to running, or blending, unstable crude diets. The program provides a framework to monitor the fouling propensity of the unit feedstock with regard to optimizing blending ratios, and/or controlling a chemical antifoulant in a feed forward manner These techniques provide a way to minimize the energy and maintenance costs associated with fouling of heat exchange equipment, as well as to select feed blends that can balance cost savings with fouling control.

It is known that the fouling tendency of hydrocarbon feedstocks, or blends thereof, can be related to the tendency for insoluble organic materials to precipitate in heat transfer equipment. The VFM of the invention measures a quantity relatable to the opaque filterable solids within a hydrocarbon sample. The automated program outlined in the present invention utilizes VFM concentration and particle size distribution data to estimate the fouling potential of a blended feedstock. This, in turn, is used to understand the blending envelope of potential hydrocarbon feeds, relate it to fouling behavior and then to provide optimal dosage of chemical treatment.

It is shown that high temperature dispersants and antifoulants are the main components in a chemical regiment used to treat process equipment, and thereby reduce the rate of fouling. There are specific chemical families that are particularly effective for use in slowing the rate of fouling in heat exchange equipment and other hot surfaces, such as furnaces. The fouling rates are affected by action of the said chemicals to colloidally stabilize the contained particulates, including asphaltenic materials. The program of the present invention is configured to allow blending stability envelopes to be ascertained prior to their use. Additionally, the program is configured to select the type and quantity of chemistry required to satisfy production requirements. Specific chemical entities include, but are not limited to, polyisobutenylphosphonic acids and esters, polyisobutenylthiophosphonic acids and esters, alkylphosphonate phenate sulfides and disulfides that may be neutralized with alkaline earth metals, or amines of polyisobutenyl succinimides, polyisobutenylsuccinate alkyl esters, magnesium or calcium salts of alkyl or dialkylnaphthelene sulfonic acids as described in U.S. Pat. No. 4,927,519 and EP Pat. No. 321424B1, herein incorporated by reference.

These antifoulant materials have been found to function at low dosages, 1-200 ppm, to prevent the undesirable deposition of insoluble material (fouling) onto surfaces in heat exchange equipment running process fluids. Fouling in heat exchangers is most generally thought to occur by first generating an unstabilized macromolecular particle that is no longer soluble in the bulk fluid, or as a colloidal species. This often occurs due to thermal stress on the hydrocarbon. Initial deposition occurs, and further destabilized species adsorb onto the site of original deposition. Bigger particles in the hydrocarbon will be more prone to contact and coalesce to the surface. Dehydrogenation of the adsorbed hydrocarbon will be driven by heat and time and make the deposit more tenacious as crosslinking reactions occur.

The dispersants are generally understood to function by a variety of mechanisms. First, the dispersant materials adsorb to the surfaces formed by growing insoluble particles and act to keep these particles small; typically less than 1 micron. Thus, the particles are more prone to continue to flow through the system and not settle on heat exchanger or other surfaces. This can be described by Stokes law, which is dependent on the radius of the particles. This is schematically shown in FIG. 9. The dispersants act by a combination of steric stabilization, which acts to repel approaching particles (dramatically increase entropy of local system and drive solvent in between particles), and blocking of polar sites on the particles which act as a driving force for coalescence. Light scattering evidence exists that shows that dispersant treated thermally stressed fluids generate particles that are up to two orders of magnitude smaller than untreated hydrocarbon fluids.

Even if the particles are not small, the above mechanism explains how the particles will be less prone to coalesce to other particles in solution, or to material already deposited on the surface.

It has also been shown that the nature of the surface plays a role in the ability of thermally stressed fluids to deposit. Metal surfaces with higher roughness, edges, or polarity are more prone to fouling. These dispersants will adsorb to such surfaces and discourage particulate or amorphous insoluble hydrocarbon from sticking to the surface.

The reaction of hydrocarbons at elevated temperatures with oxygen (even very low levels such as <5 ppm) will result in formation of polar functionalities that can drive coalescence of particulate, as well as accelerate the dehydrogenation of adsorbed hydrocarbon, which makes its removal from the surface by turbulent flow much less likely. Dispersant adsorption will block the mass transfer of the oxygen to the surface, and some of these described anti-foulants have anti-oxidant abilities by interfering with radical reactions.

In addition, hydrocarbon feed stocks, such as crude oils and their heavier distillate fractions, are thought to contain asphaltenic materials that are colloidal in nature. These colloids have highly polar and high molecular weight asphaltene species that are stabilized in the fluid by smaller resin molecules. These systems can be rendered "unstable" or prone to deposition either by thermal stress, which changes the critical ratio of the adsorbed resins to asphaltenes required to maintain a stable colloidal. The dispersants described here are believed to replace the disturbed or destroyed resins and re-stabilize the asphaltenic systems.

As described herein, the VFM measurement data provides information regarding the concentration and particle size distribution of insoluble solids in the hydrocarbon feed and/or its blends and their resultant distillate fractions. Fluids having higher amounts of solids will give a higher precipitation potential. Additionally, fluids having particle size distributions that present substantial fractions greater than a critical size threshold will also exhibit increased fouling potential. The critical size threshold varies, in a practical sense, depending upon mechanical properties of the fluid and its flow, such as viscosity, velocity and shear stress etc. Furthermore, the nature of the particles making up the distribution will also affect the fouling propensity. Finally, the feed, the particular blending ratios of individual feedstocks comprising the blend, thermal destabilization, and dehydrogenation mechanisms can all introduce solids into the system, affect the size distribution and also and the nature of the particulate matter.

Baseline performance parameters, such as fouling potential, can be established by performing a unit survey or blank test of the process unit operations and analyzing the operational data obtained from the unit survey. Based on defining a unit dependent baseline for a particular feedstock, the VFM data provides information regarding the increasing or decreasing fouling potential of the incoming feed. This information can then be used to alter chemical antifoulant injection rates. Additionally, crude blending practices are often fraught with uncertainty and significant non-linearity can occur with respect to blending ratios when considering the stability of contained asphaltenic materials and the associated fouling rates. The VFM data, when run across the desired blending envelope(s), can define regions of significant fouling potential. This can allow rational decisions to be made in real-time to adjust blending strategies to minimize fouling and/or maximize run-length.

Figure 23:
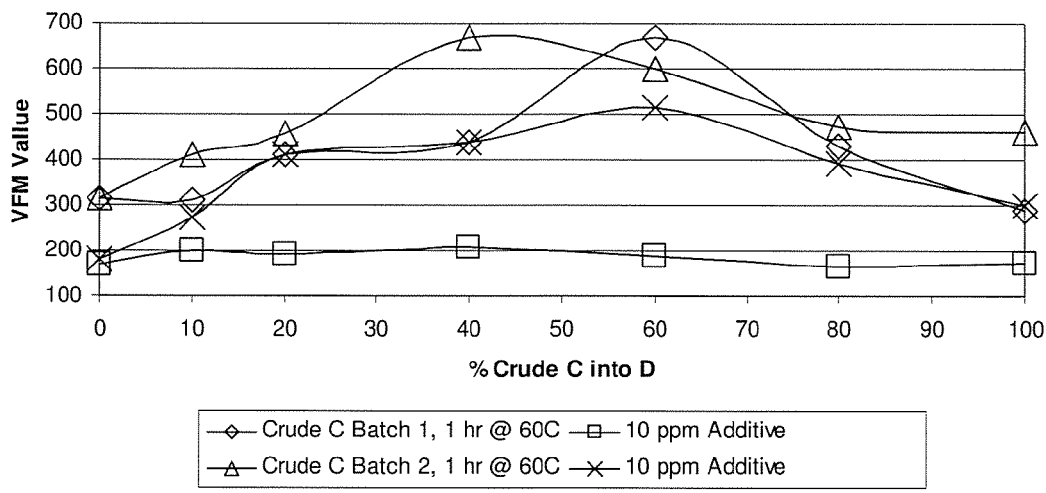
FIG. 23 is a graph illustrating VFM particle count data for a particularly asphaltenic crude (Crude D) blended into another standard crude slate (Crude E)
Figure 24:
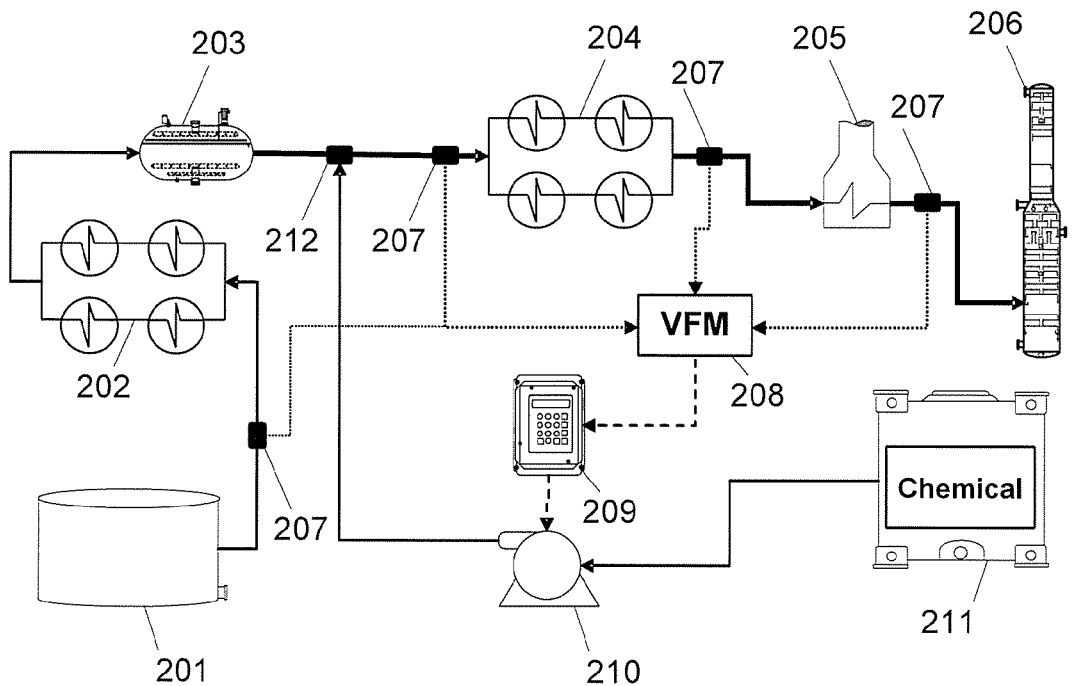
FIG. 24 is a schematic diagram illustrating how the VFM device can be used to control fouling in a process unit preheat exchanger train.

FIG. 20 and FIG. 21 show VFM particle count data for a particularly asphaltenic crude oil (Crude A) blended at several ratios with a standard crude slate (Crude B). The chart additionally shows the same blending curve with the addition of a chemical antifoulant. This set of fluids was chosen because this blend has caused severe pre-heat fouling rate increases, as well as desalter upset conditions, on multiple occasions in the past. Several important points can be noted from this data. First is that when considering the pure Crude A and Crude B data, the asphaltenic crude oil (Crude A) has much lower particle count than the normal slate (Crude B). This observation shows that the VFM can be used to evaluate incoming crude feeds to ascertain their relative fouling propensity. By performing the VFM test on these crudes after the desalting process, the intrinsic fouling propensity can be related to asphaltenic components or other inorganic contaminants which can be removed in the desalting process. Crude feedstocks and blends can be ranked as low, medium or high fouling potential feedstocks. Also notable in FIG. 21 is that upon mixing the Crude A and Crude B at varying ratios, the particle count dramatically rises for blend ratios between 40% and 60%. This shows that this blend has a tendency to exhibit a significant non-linear increase in insoluble particulate. This is likely due to the destabilization of colloidal asphaltenes as outlined above. FIG. 22 shows actual furnace inlet temperature (hereinafter "FIT") declines due to fouling as measured in the field. The FIT declined severely during several timeframes while processing crude diets having blend ratios in this problematical regime. FIG. 21 also shows that the number of insoluble particles can be dramatically affected by the addition of small amounts of chemical antifoulant. FIG. 23 shows a similar set of data for another asphaltenic crude (Crude D) blended into another standard crude slate (Crude E). The second data set is indicative of fairly widespread experience with these issues and shows that this is not something particularly related to narrow sets of crude oils.

The VFM data shown above forms the basis for the current invention in which a program is outlined to use the VFM instrument to proactively control fouling behavior in heat exchange equipment, or other pieces of process equipment prone to fouling, before problematical and costly impacts are actually experienced. By using the VFM to screen incoming crude oil, changes to the incoming particle count can be used to control chemical feed rates in combination with statistical models. By utilizing the combination of the VFM, chemical antifoulants and statistical process control methodologies, the overall program can be managed to provide an improved ability to achieve unit runtime, maintenance and economic goals. Additionally, blending strategies can be proactively developed such that great flexibility to meet overall economic goals is achieved, while preserving critical heat transfer efficiency and runtime.

An exemplary method of the invention is described, wherein the VFM device is used to control fouling in a process unit preheat exchanger train.

A process fluid enters a crude unit after being blended in a tank farm 201. It then enters a preheat system composed of a cold exchanger train 202, a desalter 203, a hot exchanger train 204, a furnace 205, and a fractionating unit 206. Fluid samples are taken at points 207 such that characteristics of the native fluid, before chemical injection, can be compared to the characteristics at various points in the system during the heating process and after chemical has been added. Fluid samples are passed to the VFM 208 and fouling propensity data is determined and compared at the various sampling points 207. VFM data is then transmitted to a processing and control mechanism 209 where mathematical analysis takes place to determine antifouling chemical demand. The analysis of the data consists of using predictive modeling techniques to evaluate the impact of chemical on fouling propensity, as measured by the VFM, and also to project theoretical run length based on the measured rate of fouling. Based upon the derived statistical parameters, necessary chemical demand is computed to maintain the fouling rate within specified limits. Instructions are then transmitted to the chemical feed pump 210, which delivers chemical from the chemical storage tank 211. Based upon the data analysis and control algorithms, an optimized dosage of antifouling chemical is injected by the injection pump 210 into the process line at injection point 212.

Other schemes can be envisioned, and this embodiment is not meant to be limiting to a specific piece of process equipment, data acquisition methodology, feed configuration, or control mechanism. One preferred embodiment might be envisioned to additionally collect data and/or inject chemical prior to tankage when raw process feed is offloaded from transportation to the refinery.

Pieces of process equipment at which a scheme similar, but not limited to, that described above could be envisioned by those skilled in the art are: fractionating unit preheat exchanger trains in the crude unit and hydrotreating unit; FCCU slurry loop exchangers and steam generators; heat exchanger equipment in delayed coking units, furnaces and reboilers throughout the refinery.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope and spirit of the disclosure as defined by the following claims.

What is claimed is:

1. A method to reduce and optimize the fouling rate in a process unit comprising the steps of:
   estimating a concentration of foulant materials contained within a fluid of the process unit;
   determining the fouling potential based on said concentration;
   determining the impact of antifoulant chemical on the fouling potential within the unit;
   determining an acceptable baseline fouling potential;
   comparing said baseline parameter to said concentration of foulant materials measured during subsequent unit operations; and
   regulating input of said anti-fouling chemical into said process unit during running of unit operations based on said comparison so as to achieve one or more unit goals.

2. A method to reduce and optimize the fouling rate in a process unit comprising the steps of:
   estimating a concentration of foulant materials contained within a fluid of the process unit;
   determining the fouling potential based on said concentration;
   determining the impact of antifoulant chemical on the fouling potential within the unit;
   determining an acceptable baseline fouling potential;
   comparing said acceptable baseline fouling potential to said fouling potential determined from said concentration of foulant materials measured during subsequent unit operations; and
   regulating input of said anti-fouling chemical into said process unit during running of unit operations based on said comparison and said impact of antifoulant chemical on said fouling potential so as to achieve one or more unit goals.

3. The method of claim 2, wherein said unit goals include improved yield, improved quality, and reduced fouling related maintenance.

4. The method of claim 3, wherein said estimating step includes estimating a distribution of foulant materials contained within said fluid; and said fouling potential is determined by said concentration and said distribution.

5. The method of claim 4, wherein said regulating step includes selecting and controlling the type or quantity of said anti-fouling chemical being input into the unit.

6. The method of claim 5, further comprising the step of improving run-lengths compared to previous un-treated conditions.

7. The method of claim 6 further comprising the use of predictive modeling to derive the impact of chemical on the fouling rate, and the amount of necessary chemical to provide adequate run length, according to planned maintenance schedules.

8. The method of claim 7, further comprising the use of multiple measurements, either within the unit or its feed steams, to determine the impact of introduced chemical upon foulant concentrations; wherein the impact of introduced chemical upon foulant concentrations is used to determine the impact of introduced chemical upon fouling potential.

9. The method of claim 8, further comprising the use of multiple chemical injection locations inside and/or outside unit boundaries.

10. The method of claim 2, wherein said estimating step is performed using an apparatus comprising:
    an optical lens system comprising a stage adapted to receive a sample of fluid;
    a light sources for focusing a beam of light onto said sample;
    means of directing said light beam along a plurality of path lengths within a predetermined area of said sample;
    means of detecting light transmitted through said sample along each path length;
    means for quantifying an intensity of said transmitted light; and
    means for correlating said quantified transmitted light to a concentration of said foulant particles in said samples.

11. The method of claim 10, further comprising means for determining the type or quantity of antifouling chemical injected into the process unit.

12. The method of claim 10, further comprising means for estimating the impact of injected anti-fouling chemical on foulant particles and run length predictions.

13. The method of claim 10, further comprising the usage of measured data to generate predictive models for use in controlling chemical injection.

14. The method of claim 10, further comprising the usage of multiple chemical injection locations inside and/or outside the units boundaries.

15. A method to improve a hydrocarbon fluid stream in a refinery comprising the steps of:
- estimating a concentration of foulant materials contained within a hydrocarbon fluid stream in a refinery;
- determining the fouling potential based on said concentration;
- determining the impact of antifoulant chemical on the foulant materials;
- determining an acceptable baseline fouling potential;
- comparing said baseline parameter to said concentration of foulant materials measured during subsequent refinery operations; and
- regulating input of said anti-fouling chemical into said fluid stream during running of refinery operations based on said comparison so as to achieve one or more refinery goals.

16. A method to improve a hydrocarbon fluid stream in a refinery comprising the steps of:
- estimating a concentration of foulant materials contained within a hydrocarbon fluid stream in a refinery;
- determining the fouling potential based on said concentration;
- determining the impact of antifoulant chemical on the fouling potential;
- determining an acceptable baseline fouling potential;
- comparing said acceptable baseline fouling potential to said fouling potential determined from said concentration of foulant materials measured during subsequent refinery operations; and
- regulating input of said anti-fouling chemical into said fluid stream during running of refinery operations based on said comparison and said impact of antifoulant chemical on said fouling potential so as to achieve one or more refinery goals.

17. The method of claim 16, wherein said refinery goals include improved yield, improved quality, improved run-lengths, and reduced fouling related maintenance.

18. The method of claim 17, wherein said estimating step includes estimating a distribution of foulant materials contained within said fluid; and said fouling potential is determined by said concentration and said distribution.

19. The method of claim 18, wherein said regulating step includes selecting and controlling the type or quantity of said anti-fouling chemical being input into the fluid stream.

20. The method of claim 19 further comprising the use of predictive modeling to derive the impact of chemical on the fouling rate, and the amount of necessary chemical to provide adequate run length, according to planned maintenance schedules.

21. The method of claim 20, further comprising: the use of multiple measurements, either within the refinery or its feed steams, to determine the impact of introduced chemical upon foulant concentrations, wherein the impact of introduced chemical upon foulant concentrations is used to determine the impact of introduced chemical upon fouling potential; and the use of multiple chemical injection locations.

22. The method of claim 21, wherein said estimating step is performed using an apparatus comprising:
- an optical lens system comprising a stage adapted to receive a sample of fluid;
- a light sources for focusing a beam of light onto said sample;
- means of directing said light beam along a plurality of path lengths within a predetermined area of said sample;
- means of detecting light transmitted through said sample along each path length;
- means for quantifying an intensity of said transmitted light; and
- means for correlating said quantified transmitted light to a concentration of said foulant particles in said samples.

* * * * *